United States Patent
Korpman et al.

(10) Patent No.: US 10,460,841 B2
(45) Date of Patent: Oct. 29, 2019

(54) INDIVIDUAL HEALTH RECORD SYSTEM AND APPARATUS

(71) Applicant: CentrifyHealth, LLC, Nashville, TN (US)

(72) Inventors: Ralph A. Korpman, Nashville, TN (US); Cindy A. Post, Colton, CA (US); Rudy R. Hilado, Leesburg, VA (US); W. Randal Clegg, Yucalpa, CA (US)

(73) Assignee: CentrifyHealth, LLC, Nashville, TN (US)

( * ) Notice: Subject to any disclaimer, the term of this patent is extended or adjusted under 35 U.S.C. 154(b) by 0 days.

(21) Appl. No.: 14/308,873

(22) Filed: Jun. 19, 2014

(65) Prior Publication Data

US 2014/0304006 A1    Oct. 9, 2014
US 2019/0065683 A9    Feb. 28, 2019

Related U.S. Application Data

(63) Continuation of application No. 14/041,769, filed on Sep. 30, 2013, now abandoned, which is a
(Continued)

(51) Int. Cl.
*G06F 19/00* (2018.01)
*G16H 50/20* (2018.01)
*G16H 10/60* (2018.01)

(52) U.S. Cl.
CPC ............. *G16H 50/20* (2018.01); *G16H 10/60* (2018.01)

(58) Field of Classification Search
USPC .......... 705/2–4; 707/794, E17.009, 600–606
See application file for complete search history.

(56) References Cited

U.S. PATENT DOCUMENTS 5,701,400 A    12/1997  Amado
5,724,575 A    3/1998   Hoover et al.
(Continued)

FOREIGN PATENT DOCUMENTS

WO    02/31738 A1       4/2002
WO    2002/031739 A1    4/2002

OTHER PUBLICATIONS

Paterson, Grace I. "Boundary infostructures for chronic disease." (2007).*

(Continued)

*Primary Examiner* — Mark Holcomb
(74) *Attorney, Agent, or Firm* — Alston & Bird LLP

(57) ABSTRACT

A system, apparatus, and related methods for the collection, processing, evaluation, transformation, and reporting of individual health care information from diverse information systems and sources. A individual health record (IHR) of the present invention provides a structure for individuals to participate in, and manage, their health and their medical care, while still meeting the needs of health care organizations and caregivers. An IHR object may be formed by obtaining information from diverse health care information systems and sources, and transforming and re-purposing into a coherent account of the individual's overall health and care using a comprehensive health care ontology. As information from various sources is updated or available, the IHR is dynamically updated on a continuous or periodic basis. In one embodiment, the IHR system is contained in a self-contained package or "appliance" designed to "plug and play" in existing health care information technology systems and networks, with minimal effort and intervention.

25 Claims, 39 Drawing Sheets

Related U.S. Application Data continuation of application No. 12/723,753, filed on Mar. 15, 2010, now Pat. No. 8,560,348, which is a continuation-in-part of application No. 11/862,192, filed on Sep. 26, 2007, now Pat. No. 10,127,620.

(60) Provisional application No. 60/826,967, filed on Sep. 26, 2006.

(56) References Cited

U.S. PATENT DOCUMENTS

| | | | |
|---|---|---|---|
| 5,937,409 | A | 8/1999 | Wetherbee |
| 6,104,963 | A * | 8/2000 | Cebasek et al. ............... 700/86 |
| 6,163,781 | A | 12/2000 | Wess, Jr. |
| 6,272,468 | B1 | 8/2001 | Melrose |
| 6,314,556 | B1 | 11/2001 | Debusk et al. |
| 6,519,605 | B1 | 2/2003 | Gilgen et al. |
| 6,533,724 | B2 | 3/2003 | McNair |
| 7,349,859 | B1 | 3/2008 | Lamer et al. |
| 7,533,030 | B2 | 5/2009 | Hasan et al. |
| 7,720,691 | B2 | 5/2010 | Hasan et al. |
| 8,412,541 | B2 * | 4/2013 | Qian et al. ........................ 705/3 |
| 2001/0051881 | A1 | 12/2001 | Filler |
| 2002/0103811 | A1 * | 8/2002 | Fankhauser ........... G06F 19/322 |
| 2003/0055679 | A1 | 3/2003 | Soll et al. |
| 2003/0172368 | A1 * | 9/2003 | Alumbaugh et al. ......... 717/106 |
| 2004/0078217 | A1 | 4/2004 | Bacevice et al. |
| 2004/0122706 | A1 | 6/2004 | Walker et al. |
| 2004/0225629 | A1 | 11/2004 | Eder |
| 2005/0228808 | A1 | 10/2005 | Mamou et al. |
| 2005/0273367 | A1 | 12/2005 | Nourie et al. |
| 2006/0010011 | A1 | 1/2006 | Ullom et al. |
| 2006/0020466 | A1 * | 1/2006 | Cousineau et al. ........... 704/257 |
| 2006/0020493 | A1 * | 1/2006 | Cousineau et al. ............... 705/2 |
| 2006/0052945 | A1 * | 3/2006 | Rabinowitz et al. ........... 702/20 |
| 2006/0112029 | A1 | 5/2006 | Estes |
| 2007/0005621 | A1 | 1/2007 | Lesh et al. |
| 2007/0016450 | A1 * | 1/2007 | Bhora et al. ....................... 705/3 |
| 2007/0083607 | A1 | 4/2007 | Thompson et al. |
| 2007/0106753 | A1 | 5/2007 | Moore |
| 2007/0118399 | A1 | 5/2007 | Avinash et al. |
| 2007/0250405 | A1 | 10/2007 | Ronen et al. |
| 2008/0040151 | A1 | 2/2008 | Moore |
| 2008/0134133 | A1 | 6/2008 | Dellostritto et al. |
| 2012/0215560 | A1 | 8/2012 | Ofek et al. |

OTHER PUBLICATIONS

Webster A Methodology for incorporating web technologies into a computer-baesd patient record, Int'l J Medical Informatics, vol. 68, Issues 1-3, Dec. 2002, pp. 39-47; available at https://doi.org/10.1016/S1386 5056(02)00062-X.

Perez-Rey, D. et al. "Ontofusion: Ontology-based Integration of Genomic and Clinical Databases", Jul. 1, 2006, Computers in Biology and Medicine, pp. 712-730, vol. 36, No. 7-8.

Paterson, G. I. (2007). Boundary infostructures for chronic disease. (Order No. NR27167, Dalhousie University (Canada)). ProQuest Dissertations and Theses, , 183-n/a. Retrieved from http://search.proquest.com/docview/304792954?accountid=14753. (304792954).

Outgoing Written Opinion of the ISA dated Mar. 13, 2008 for WO Application No. PCT/US07/079609.

Outgoing—ISA/210—International Search Report dated Mar. 13, 2008 for WO Application No. PCT/US07/079609.

Notice of Allowance and Fees Due (PTOL-85) dated Sep. 12, 2018 for U.S. Appl. No. 11/862,192.

Notice of Allowance and Fees Due (PTOL-85) dated Jul. 11, 2018 for U.S. Appl. No. 11/862,192.

Notice of Allowance and Fees Due (PTOL-85) dated Aug. 28, 2013 for U.S. Appl. No. 12/723,753.

Non-Final Rejection dated Oct. 12, 2011 for U.S. Appl. No. 12/723,753.

Non-Final Rejection dated Nov. 28, 2016 for U.S. Appl. No. 14/937,354.

Non-Final Rejection dated Nov. 12, 2014 for U.S. Appl. No. 11/862,192.

Non-Final Rejection dated Jan. 28, 2015 for U.S. Appl. No. 14/041,769.

Non-Final Rejection dated Jan. 10, 2018 for U.S. Appl. No. 14/937,354.

Non-Final Rejection dated Aug. 10, 2010 for U.S. Appl. No. 11/862,192.

Non-Final Rejection dated Aug. 1, 2017 for U.S. Appl. No. 11/862,192.

Non-Final Rejection dated Apr. 27, 2018 for U.S. Appl. No. 14/792,330.

Non-Final Rejection dated Apr. 23, 2013 for U.S. Appl. No. 12/723,753.

Non-Final Rejection dated Apr. 22, 2013 for U.S. Appl. No. 11/862,192.

Non-Final Rejection dated Apr. 5, 2016 for U.S. Appl. No. 11/862,192.

Kerkri, E. M. et al. "An Approach for Integrating Heterogeneous Information Sources in a Medical Data Warehouse", Jan. 1, 2001, Journal of Medical Systems, pp. 167-176, vol. 25, No. 3.

ISA/220—Notification of Transmittal or Search Report and Written Opinion of the ISA, or the Declaration dated Mar. 13, 2008 for WO Application No. PCT/US07/079609.

Final Rejection dated Oct. 9, 2015 for U.S. Appl. No. 14/041,769.
Final Rejection dated Nov. 28, 2017 for U.S. Appl. No. 11/862,192.
Final Rejection dated Nov. 23, 2016 for U.S. Appl. No. 11/862,192.
Final Rejection dated Jun. 7, 2012 for U.S. Appl. No. 12/723,753.
Final Rejection dated Jun. 4, 2015 for U.S. Appl. No. 11/862,192.
Final Rejection dated Feb. 6, 2019 for U.S. Appl. No. 14/792,330.
Final Rejection dated Feb. 4, 2011 for U.S. Appl. No. 11/862,192.
Final Rejection dated Dec. 6, 2013 for U.S. Appl. No. 11/862,192.
Final Rejection dated Aug. 25, 2017 for U.S. Appl. No. 14/937,354.

Contributors, "Portal (Informatik)", Aug. 8, 2016, Wikipedia: The Free Encyclopedia, 12 pages, URL:https://de.wikipedia.org/w/index.php?title=Portal_(Informatik)&oldid=19941205, Sep. 17, 2018.

Contributors, "Ontologie (Informatik)", Sep. 21, 2006, Wikipedia: The Free Encuyclopedia, 17 pages, URL:https://de.wikipedia.org/w/index.php?title=Ontologie_(Informatik)&oldid=21741585, Sep. 17, 2018.

Chong, Q. et al., "Ontology Based Metadata Management in Medical Domains", May 1, 2003, Journal of Research and Practice in Information Technology, pp. 139-153, vol. 35, No. 2.

Applicant Initiated Interview Summary (PTOL-413) dated Jul. 2, 2013 for U.S. Appl. No. 12/723,753.

Applicant Initiated Interview Summary (PTOL-413) dated Apr. 4, 2013 for U.S. Appl. No. 12/723,753.

* cited by examiner

CHIS Message: CentriHealth Interface Schema message
The CHIS Message provides a consistent but flexible data structure of bringing in data from multiple source systems

How Does the IHR Use Rules?

- to instantiate health care guidelines such as health screening, HEDIS and Pay-for-Performance indicators.
- to categorize individuals and Users
- to update/notify individual's health status
- to generate health maintenance actions
- to process action plans
- to create data from other data
- to perform data entry business logic
- to protective monitoring
- to perform data entry edit checks
- to select appropriate ontology CHID
- to application flow
- to display personalized content

FIGURE 31

Rule Categories

| Rule Category | Rule Category |
|---|---|
| Acute Bronchitis Treatment | Hypertension Screening |
| Asthma Treatment | Hypertension Management |
| BMI | IHR Access |
| Breast Cancer Screening | Immunization-Adult |
| Cervical Cancer Screening | Immunization Childhood |
| Chlamydia Screening | Nephropathy Screening |
| Cholesterol Screening | Obesity Screening |
| Cholesterol Management | Osteoporosis Screening |
| Colorectal Cancer Screening | Osteoporosis Treatment |
| Diabetes Screening | Prenatal Screening |
| Diabetes Management | Retinopathy Screening |
| End Stage Renal Disease Management | Tobacco Screening |
| Glaucoma Screening | Tobacco Cessation |

FIGURE 32

Rule Types

- Assertions: concept definitional rules
- Compliance: evaluates multiple findings to determine whether compliant or not compliant with guideline
- Enrollment/Disenrollment: evaluates demographics, relationships and health issues to create finding
- Finding: evaluates multiple findings and makes another finding
- IHR Access: evaluates of user has accessed IHR with defined time
- Result-Finding: takes result + result value and makes a finding
- Service Performance: evaluates was test/exam/procedure performed within define time limit (Up-To-Date, Not-Up-To-Date, Unknown)
- Service Performance Offset: evaluates was test/exam/procedure performed within time span

Vistar Physician Portal

The Vistar physician portal provides a personalized, convenient and secure means of viewing patient information over the Internet. Any physician in the community can view their patients's data. The Vistar portal provides you with:

- multiple views patient data from any source
- the ability to communicate with your patients and colleague
- up-to-date health status on each patient
- with reminders for patient *followup*
- the ability to view medication history *prescription* compliance

Secure Message Action

Health Summary

⊕ John Baker   Gender: Male   Birth Date: 04 Oct 1943
Age: 64 yr
You are here: Health Summary                  ⟳ Refresh Health Summary                ⊠ Select Individual ⊕ Health Status ⊖ Reminders/Follow-up

Reminder Rule

| Date | Calendar Event | Status |
|---|---|---|
| 07 Sep 2007 | Colorectal Cancer Screening Reminder | |
| 07 Sep 2007 | Blood Pressure Reminder | |
| 07 Sep 2007 | LDL Cholesterol Reminder | |
| 07 Sep 2007 | Microalbumin Reminder | |
| 07 Sep 2007 | HbA1c Reminder | |
| 24 Sep 2007 | Eye Exam Reminder | |

Pages:

⊕ Care Team

⊖ Health Conditions

| Condition ▲ | Status | Onset Date | Last Activity/Update | Source |
|---|---|---|---|---|
| Anemia | | | | Express Scripts Pharmacy Claims |
| Atherosclerotic Cardiovascular Disease | Active | | | Clinical Work Station |
| Bladder-Neck Obstruction | Active | | | Clinical Work Station |
| Diabetes Mellitus – Type II | Active | | | Clinical Work Station |

Inbox

You are here: Inbox

| | | | | | | |
|---|---|---|---|---|---|---|
| Inbox | | 🗑 Delete Selected Items | | | ⟳ Refresh Inbox | |
| | Received Date ▼ | Subject | Sent By | Size | Flags | |
| ☐ | 07 Nov 2007 09:51 PM | Welcome! | system | 1 KB | Draft, Seen | |
| ☐ | 07 Nov 2007 09:49 | November 4, 2007 EKG Results | Mark Green | 1 KB | Draft, Seen | |

Compliance Rule

Health Status

You are here: Health Status

⊙ Refresh This View  ⊙ Help

⊕ John Baker   Gender: Male   Birth Date: 03 Oct 1943   Age: 65 yr

∴ Choose New Individual

Health Status Summary Information

The Health Status Summary lists the current status on an individual's health conditions. This summary contains the programs, (e.g., Diabetes Management, Women's Preventative Health) in which the individual is currently listed, along with a current status on each of the measures included in the programs. The Health Status Summary also lists the current status of compliance with the care guidelines defined for the individual.

⊕ Sexual Function                                                       ⊙ Tell Me More
⊕ Sensory Status: Hearing and Vision                                    ⊙ Tell Me More
⊕ Immunization Status                                                   ⊙ Tell Me More
⊕ Colorectal Cancer Screening Group
⊖ HEDIS Compliance

| Goal | Status | Alert | Recommendation | Last Update |
|---|---|---|---|---|
| Annual HbA1c Exam | Overdue | ● | ⊙ Patient has exceeded Hb A1c guideline. | 09 May 2008 |
| HEDIS Diabetes Blood Pressure Control <130/80 mmHg | Not Compliant | ● | Patient has exceeded BP guideline of <130/80 and within one year. | 09 May 2008 |
| HEDIS HbA1c Control | Poor Control | ● | Alert: Your patient either has not had a Hemoglobin A1c test within the last year or the level was >9%. | 09 May 2008 |
| HEDIS Cholesterol Management for Patients with Cardiovascular Conditions Guideline | Abnormal | ● | Patient is not in compliance with recommended cholesterol screening guidelines. | 09 May 2008 |
| HEDIS Diabetes Comprehensive Care | Not Compliant | ● | ⊙ Patient has not met HEDIS Diabetes status guidelines. | 09 May 2008 |
| HEDIS Nephropathy Screening | Not Compliant | ● | Patient is not compliant with nephropathy screening guidelines. | 09 May 2008 |
| HEDIS LDL Cholesterol Screening Guideline | Not Compliant | ● | ⊙ Patient has exceeded LDL Cholesterol guideline. | 09 May 2008 |
| HEDIS Retinopathy Screening | Compliant | ● | Retinal Exam guideline met. Remind patient to continue this practice. | 15 Oct 2006 |
| HEDIS Colorectal Cancer Screening | Compliant | ● | ⊙ Patient is compliant with colorectal cancer screening guidelines. | 15 Jan 2002 |

FIGURE 37

Creating a Rule

- Rule Identification:
  *Annual Mammogram Exam Status Rule* IHR123589

- Rule Type: Service Performance
- Selection Criteria:
  *USPHT Breast Cancer Screening Group*
  *HEDIS Breast Cancer Screening Enrolled Group*
  [i.e., Gender = Female + Age = 50 – 65]

- Evaluation Parameters
  - Service: *Annual Mammogram* IHR123589
  - Days Check: 365

- Action(s) Taken
  - Actions take place if all the conditions are "true"

*Up-to Date Finding:* Annual Mammogram Exam Screening Status Up-to-Date IHR259675
  *Not-Up-to Date Finding:* Annual Mammogram Exam Screening Status Not-Up-to-Date IHR259676
  *Unknown Finding:* Annual Mammogram Exam Screening Status Unknown IHR259677

FIGURE 38

INDIVIDUAL HEALTH RECORD SYSTEM AND APPARATUS

This application is a continuation of U.S. application Ser. No. 14/041,769, filed Sep. 30, 2013, by Ralph A. Korpman, et al., which is a continuation of U.S. application Ser. No. 12/723,753, filed Mar. 10, 2010, by Ralph A. Korpman, et al, which is a continuation-in-part of U.S. application Ser. No. 11/862,192, filed Sep. 26, 2007, by Ralph A. Korpman, et al., which claims benefit of U.S. Provisional App. No. 60/826,967, filed Sep. 26, 2006, by Ralph A. Korpman, et al., and is entitled to those filing dates for priority in whole or in part. The specification, attachments, drawings and complete disclosures of U.S. application Ser. Nos. 12/723,753 and 11/862,192, and U.S. Provisional App. No. 60/826,967, are incorporated herein in their entireties by specific reference for all purposes.

FIELD OF INVENTION

This invention relates to a system, apparatus, and associated methods for the collection, processing, evaluation, transformation, and reporting of individual health care information from diverse information systems and sources.

BACKGROUND OF THE INVENTION

Most information technology (IT) applications are built on predefining, with great specificity, the types and construction of information to be received, sent, processed, and stored by the IT service or application. For many industries, this model works fairly well. In the health care industry, this model may work passably well when the application is used in operating a particular institution or practice where the relevant information is fairly limited, and can be specifically defined, collected, and managed. Even in such limited circumstances, however, such applications have problems because of the inherent randomness in biologic functions. This inherent unpredictability of biologic functions means that an individual's health does not follow a predefined course, making it a particularly difficult automation challenge.

This model does not work well for an individual-centric approach to health care. Health care is transforming from a traditional, provider-centric, organizational-driven approach to an individual-centered system. This individual-centered approach cuts across all providers and patients, and the interrelationships of sources of information cannot be predicted in advance. In addition, the information and relationships will vary widely from person to person, place to place, and time to time. Furthermore, because a broad range of patients, practitioners, and other health care stakeholders will be accessing and using the information for a variety of purposes, not only are the sources not predefined, but uses of the information are not predetermined either. Attempting to create a comprehensive, workable system for handling individual health care records using current models results in enormous, unwieldy databases and applications that are expensive and slow to operate and maintain, and prevent such systems from fulfilling their functions.

Accordingly, what is needed is a new model and approach to creating and maintaining individual health records that is robust and flexible enough to handle health information from a wide variety of unpredictable sources, and permits a broad range of patients, practitioners, and other users to manipulate and use health information in a wide variety of unpredictable ways.

SUMMARY OF THE INVENTION

The present invention is a system, apparatus, and related methods for the collection, processing, evaluation, transformation, and reporting of individual health care information from diverse information systems and sources. Health care is transforming from a traditional, provider-centric, organizational-driven approach to an individual-centered system. The individual health record (IHR) of the present invention provides a structure for individuals to participate in, and manage, their health and their medical care, while still meeting the needs of health care organizations and caregivers, thereby supporting collaborative care in a new way.

The IHR is formed by obtaining information from diverse health care information systems and sources, including, but not limited to, existing systems and information flows such as employee health records, pharmacies, laboratories, and medical claims information streams. The information from these sources is transformed and re-purposed into a coherent account of the individual's overall health and care. The IHR is not a simple collection of all health care information about the individual; instead, the information is processed by means of an individual health information model that incorporates a comprehensive health care ontology.

In one exemplary embodiment, information is received from a source, validated, parsed, transformed, matched to an existing individual, and assigned an ontology concept code. Next, a message object is created, the data is repurposed or recontextualized, subjected to a rules evaluation, and filed in an IHR database. As information from various sources is updated or available, the IHR is dynamically updated on a continuous or periodic basis. A Single Best Record (SBR) of information may be created.

In other exemplary embodiments, the invention provides ways and means to interact with the information in the IHR in a variety of ways, including through health portals, portlets, and web services. It allows individuals to understand and participate in their health care, and enables caregivers and consumers to collaborate and interact using the same record in different ways. It embraces the emerging roles of custodian and health care advocate, and assists health care stakeholders, including but not limited to health systems, health plans, IPAs, RHIOs, employers, providers, and individuals, to meet the requirements and needs for health care systems going forward into the future. In one exemplary embodiment, the present invention does not replace existing information systems and infrastructure; instead, it provides a standards-based, service-oriented infrastructure that rapidly and easily provides health-related information and components that work with such existing systems.

In another exemplary embodiment, the IHR system is contained in a self-contained package or "appliance." The IHR appliance is designed to "plug and play" in existing health care information technology systems and networks, with minimal effort and intervention. Information is obtained from all available source systems and dynamically constructed into the IHR.

DESCRIPTION OF THE DRAWINGS

FIG. 31 is chart of exemplary rule uses.

FIG. 32 is a table of exemplary rule categories.

FIG. 33 is a list of exemplary rule types.

Figure 34:
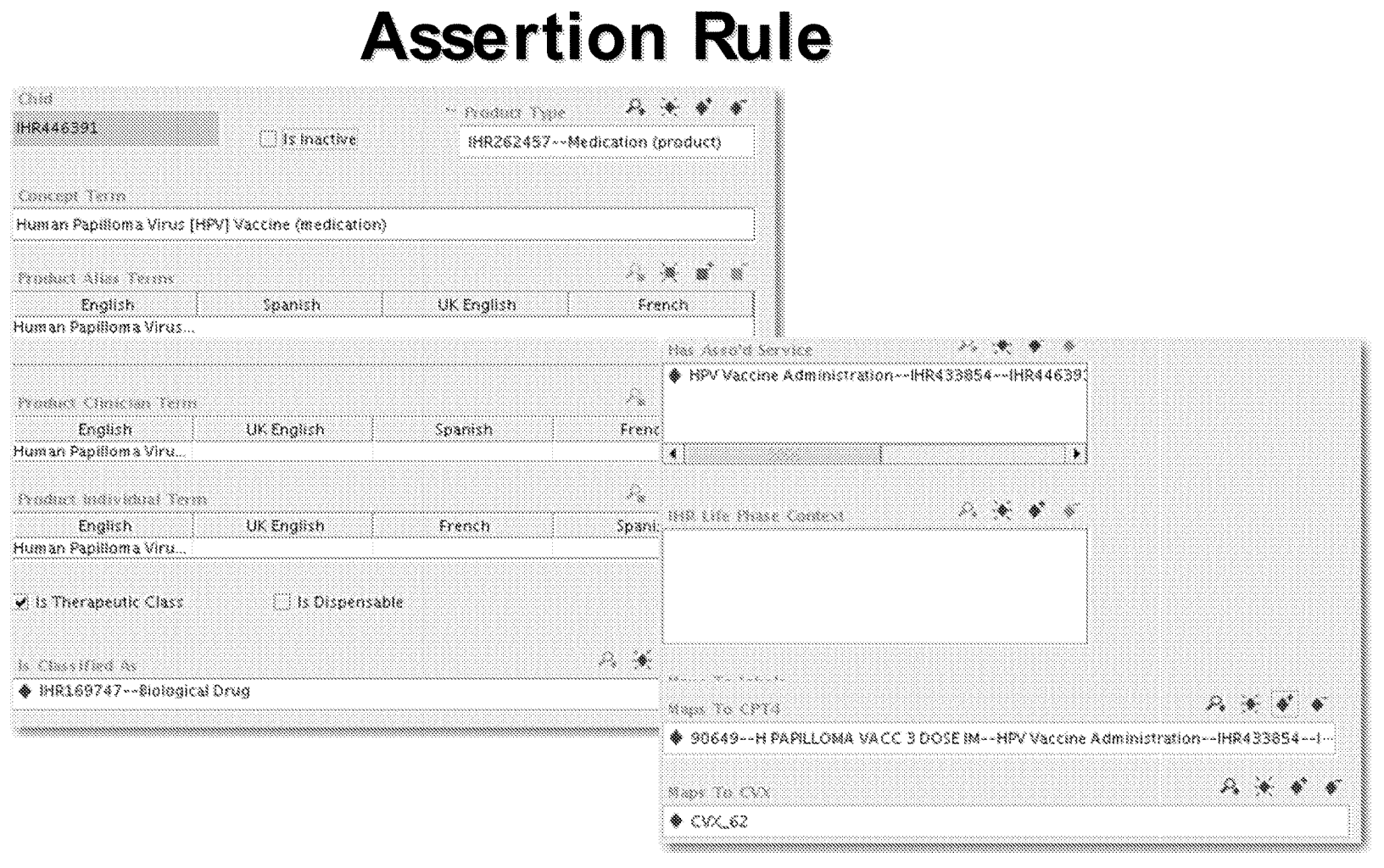
Figure 36:
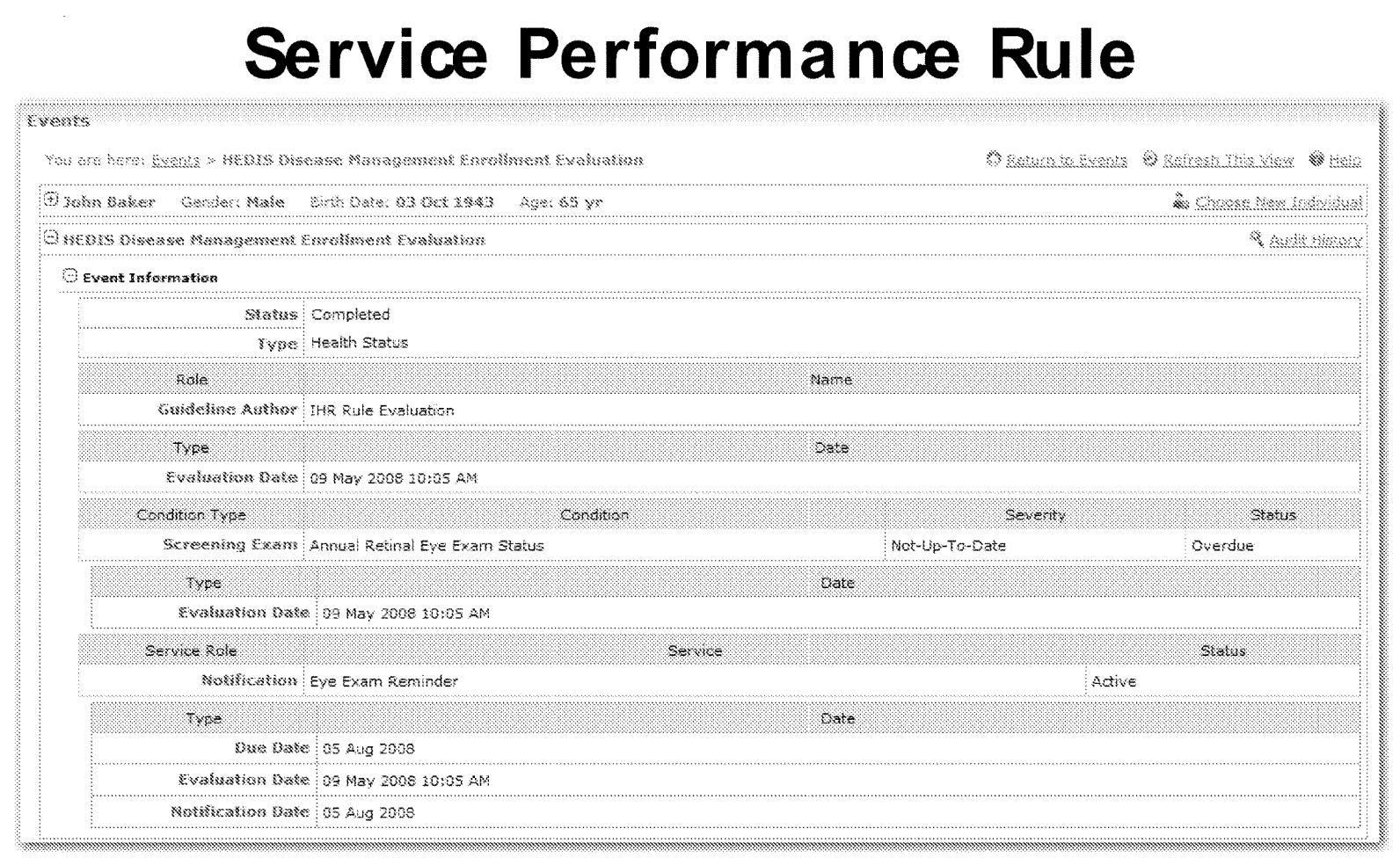

FIGS. 34 through 37 are screenshots of various rule examples.

FIG. 38 illustrates an example of a rule creation process.

DETAILED DESCRIPTION OF EXEMPLARY EMBODIMENTS

Figure 1:
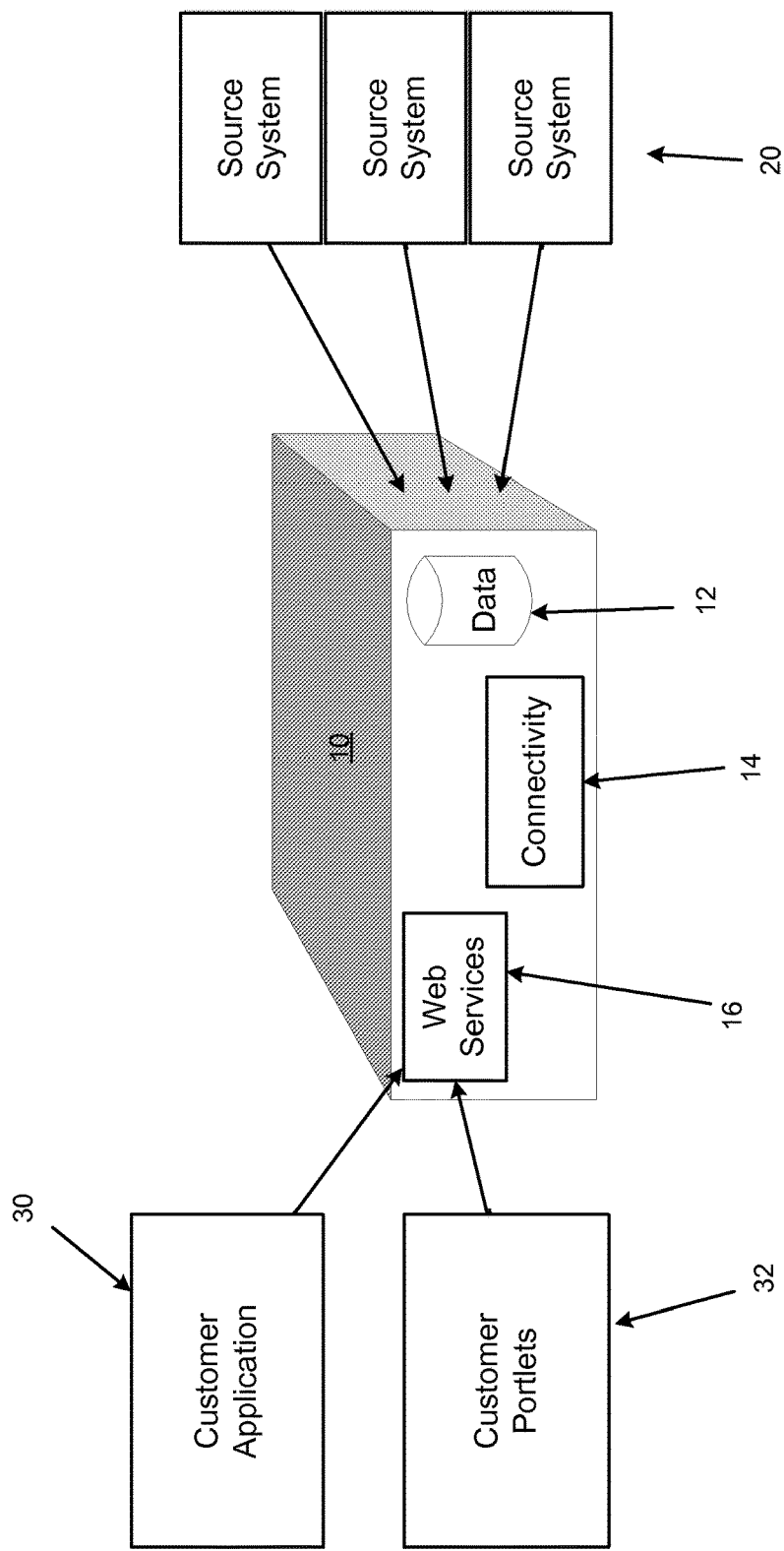
FIG. 1 is an overview of an IHR system in accordance with one embodiment of the present invention.

The present invention is a system, apparatus, and related methods for the collection, processing, evaluation, transformation, and reporting of individual health care information from diverse and potentially unpredictable information systems and sources, which also allows a wide variety of patients, health care givers, practitioners, and other users to manipulate and use the information in a variety of potentially unpredictable ways. The individual health record (IHR) system of the present invention provides a structure for individuals to participate in, and manage, their health and their medical care, while still meeting the needs of health care organizations and caregivers, thereby supporting collaborative health care in a new way.

The present invention uses a new business object model approach, known as Health Universal Genericity (HUG). This approach presumes that received information can be represented by a handful of highly abstracted health objects. These abstractions include, but are not limited to, health events, health conditions, health services, health products, and health relationships. Individual objects are created from data shared among these abstracted health objects through the unique interplay of "data objects," which exist only to hold data in support of the IHR-supported health delivery process. Each object's attributes are a composite of specific variables defined in the object class, extended by non-programmatically supported user-defined attributes.

In one exemplary embodiment, the IHR is formed by obtaining information from diverse health care information systems and sources, including, but not limited to, existing systems and information flows such as employee health records, pharmacies, laboratories, and medical claims information streams. The information from these sources is transformed and re-purposed into a coherent account of the individual's overall health and care. The IHR is not a simple collection of all health care information about the individual; instead, the information is processed by means of an individual health information model that incorporates a comprehensive health care ontology.

The system of the present invention has several unique characteristics that distinguish it from prior art systems. First, the level of abstraction is far higher than has been generally used in health care. High level abstract objects appropriate to each individual's health care are used, rather than the specific, detailed objects specific to each care setting used in the prior art. The use of these high level abstract objects in the present invention allows broad adaptability and flexibility without the intervention of programming modifications and resources that would required to effect changes in other systems. Second, the extension of the object model by binding it to the comprehensive health care ontology changes the meaning and use of the traditional object paradigm. Third, the system can take potentially all information about an individual (including, but not limited to, clinical, financial, personal, health, and administrative information), and represent it in a single, unified fashion. The system thereby can tie together not only the matching clinical-to-clinical or financial-to-financial transactions, but transactions or interactions across these traditionally separate data streams as well. This presents a uniquely robust view of each individual, his or her health care status, and the relationships of the health care system. Fourth, the system has the ability to extend the health objects, and their behavior, by modifying the ontology rather than the objects themselves. This modification can be done non-programmatically, thereby providing increased installability and flexibility over the prior art. Fifth, the creation of a health object from a metadata data object by the process of "centrification" (as discussed in more detail below) allows both preservation of the source information and simultaneous repurposing or recontextualizing of the information to a uniform and unified representation. It should be noted that the system of the present invention does not use an XML-like approach, where data fields and their definitions are stored as pairs but the underlying infrastructure knows nothing about either part; in the case of the present invention the infrastructure is fully informed regarding both parts.

In one exemplary embodiment, the set of healthcare objects are unique, and allow virtually any health instance or activity to be characterized and interrelated to other health information known about, or to be known about, about an individual. Each object may comprise methods, attributes, and inheritances.

Figure 2:
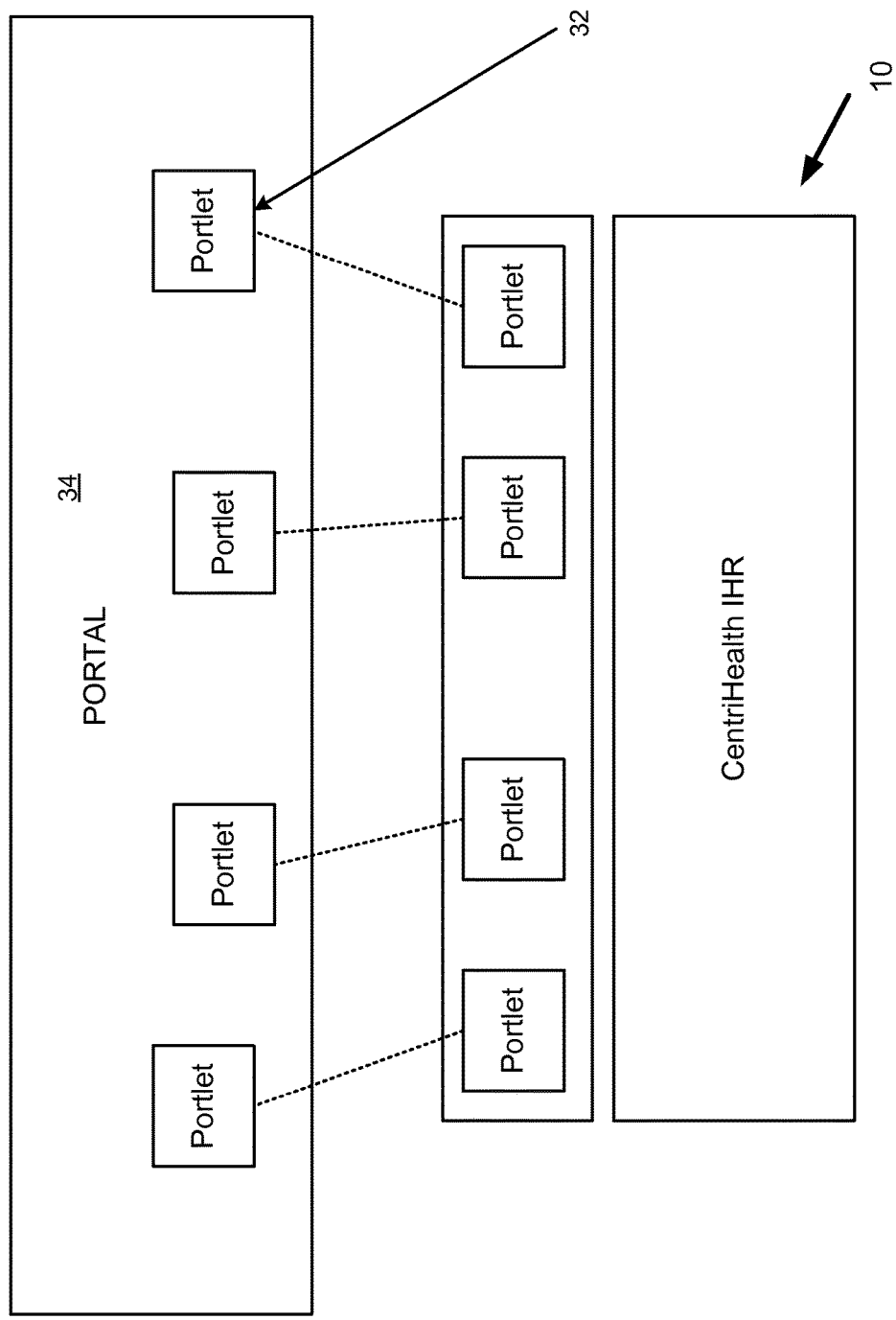
FIG. 2 is a diagram of customer portlets in a customer portal in accordance with an embodiment of the present invention.

FIG. 1 shows a broad, abstract view of an IHR system. The core IHR application 10 comprises the health data 12, connectivity services 14, and Internet Web services 16. Data is received from a variety of source systems 20. A variety of different types of users can access the IHR system through customer applications 30 or customer portlets 32 (described in more detail below). Customer portlets 32 may be used in customer portals 34, as shown in FIG. 2.

Figure 3:
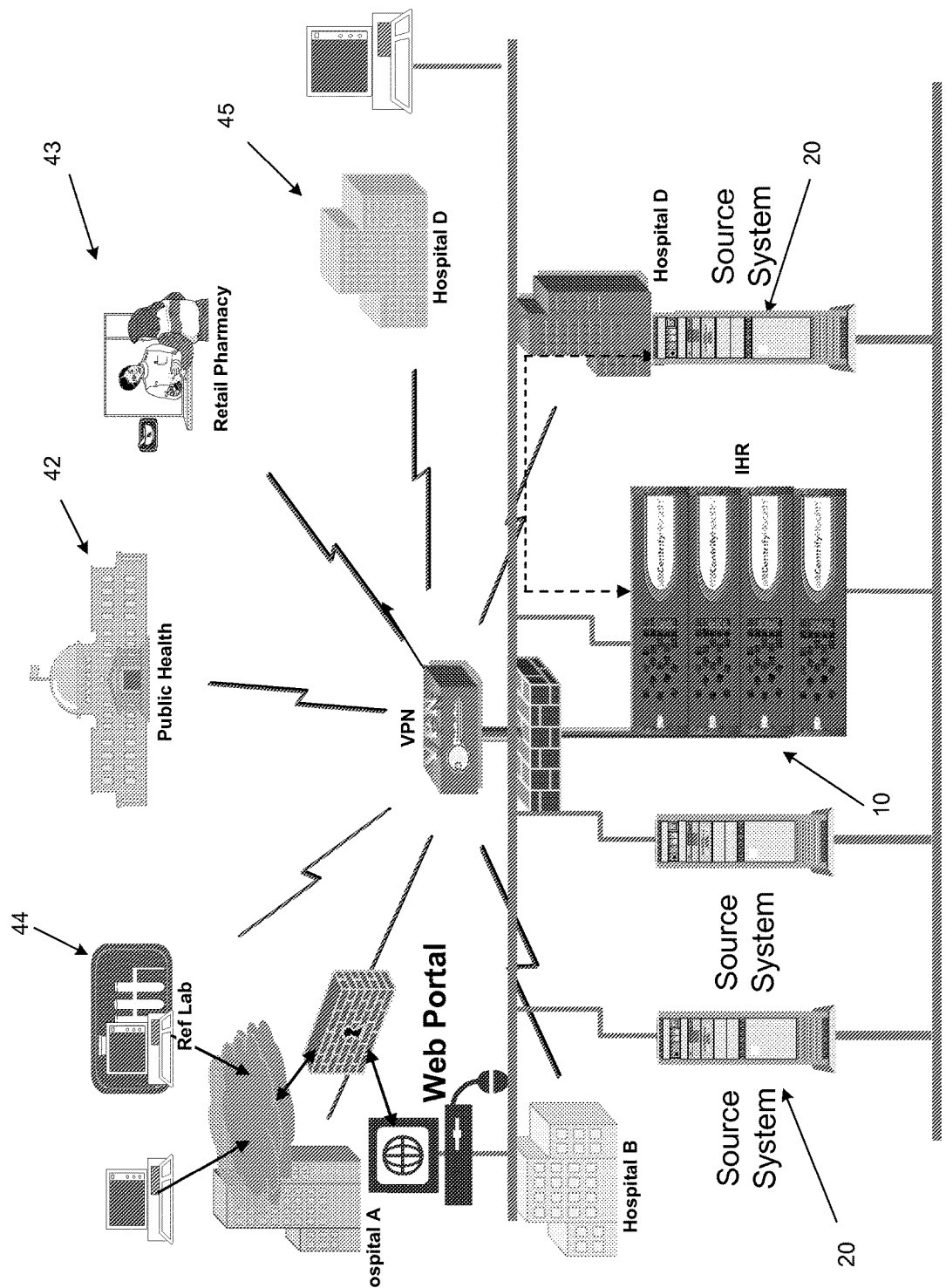
FIG. 3 is another view of an IHR system in accordance with one embodiment of the present invention.
Figure 17:
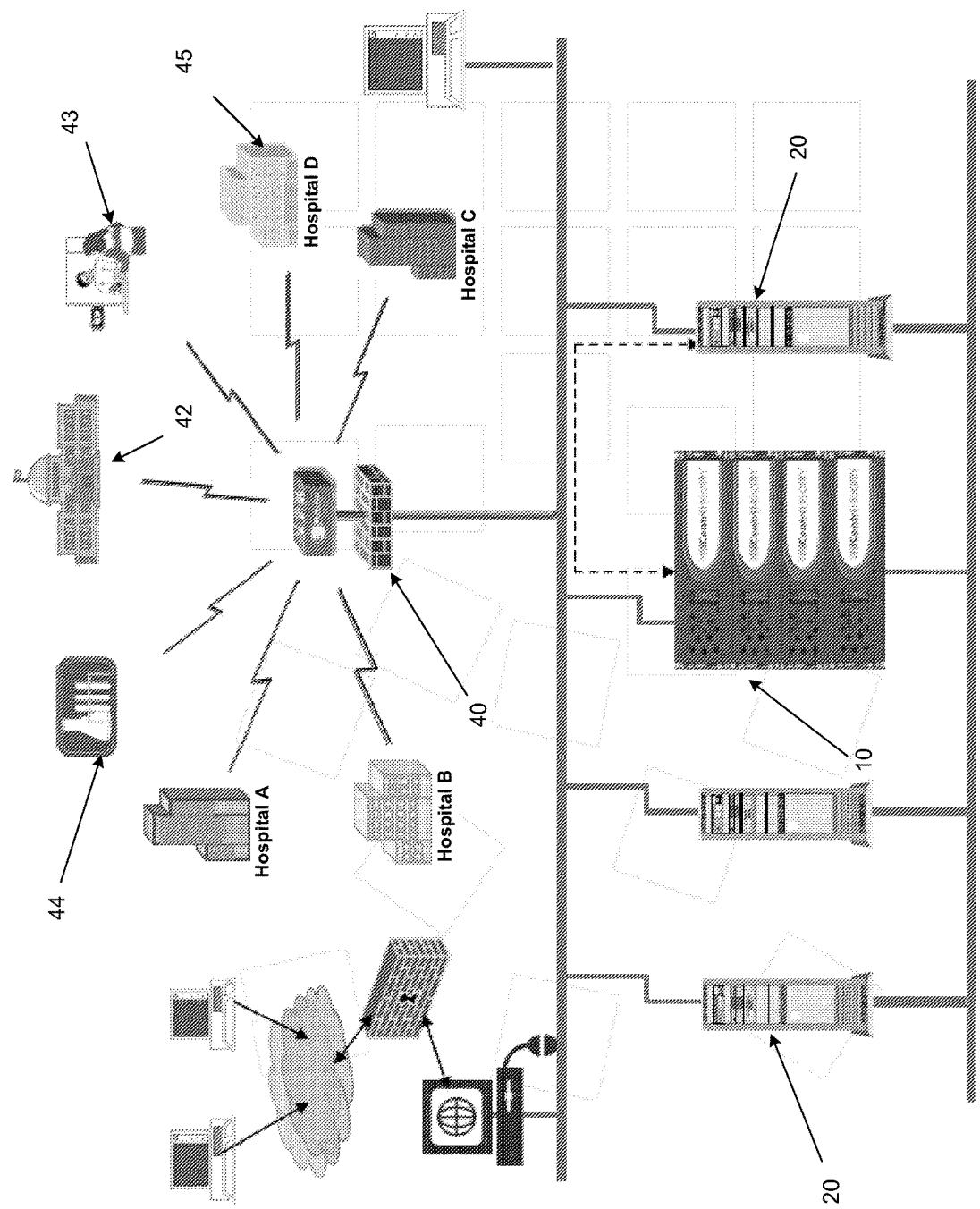
FIG. 17 is another view of an IHR system in accordance with one embodiment of the present invention.

FIGS. 3 and 17 show the IHR application 10 as an appliance installed in a customer's existing IT system behind a firewall 40. Information is received from a variety of source systems 20. Users include, but are not limited to, public health entities 42, retail pharmacies 43, labs 44, and hospitals 45.

Figure 4:
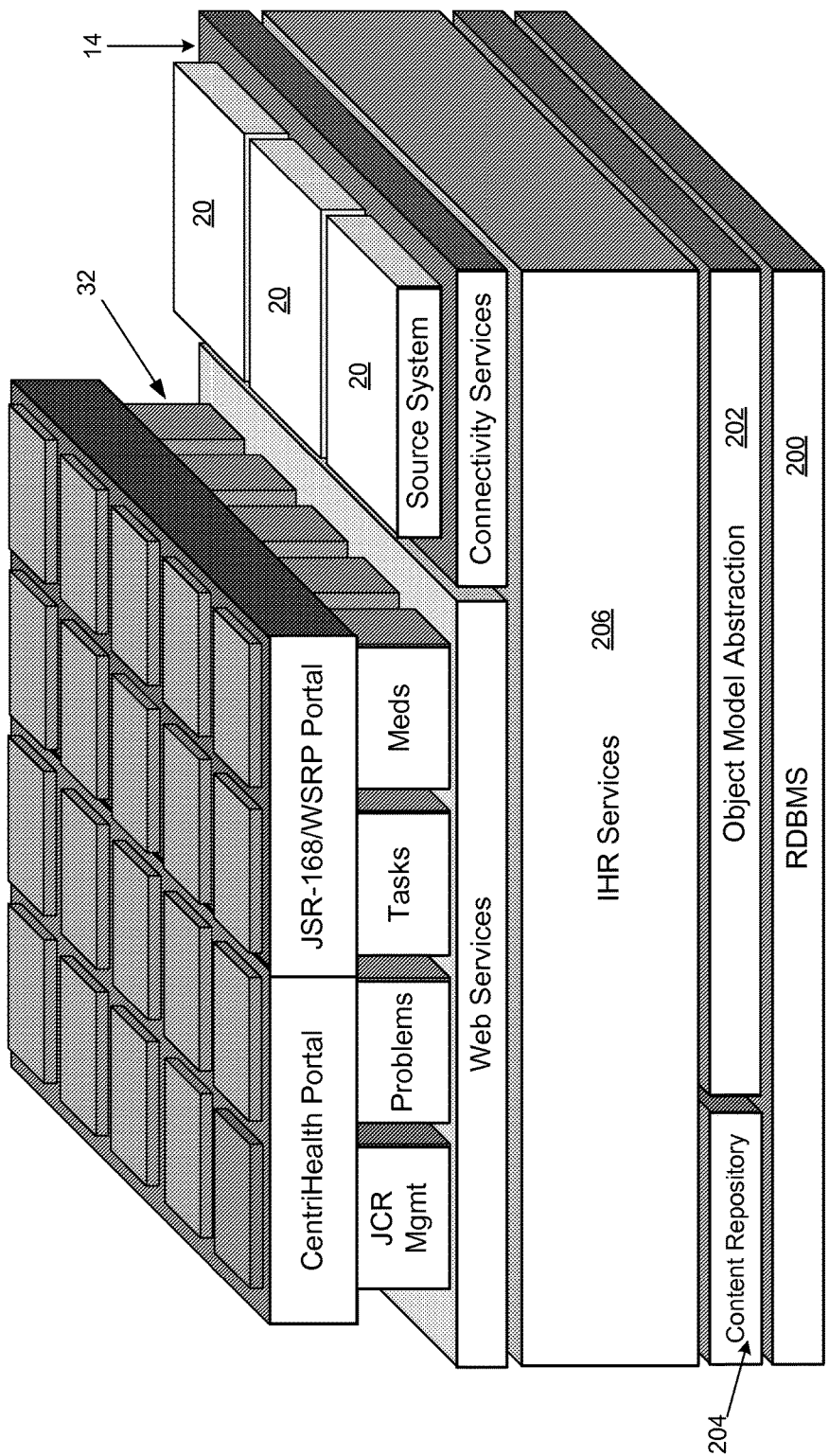
FIG. 4 is yet another view of an IHR system in accordance with one embodiment of the present invention.
Figure 18:
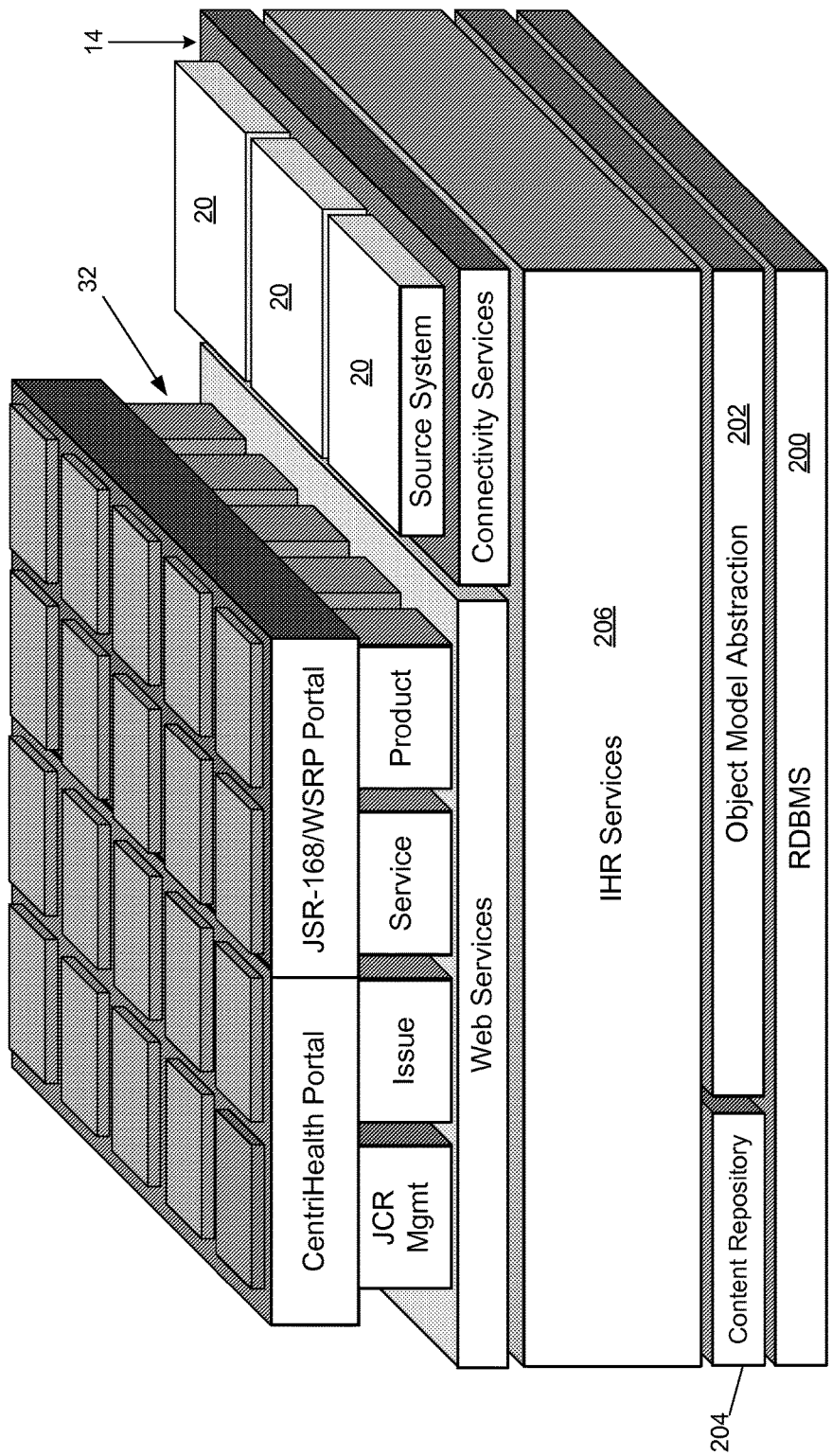
FIG. 18 is yet another view of an IHR system in accordance with one embodiment of the present invention.

In one exemplary embodiment, as shown in FIGS. 4 and 18, the IHR system comprises a persistent data storage layer 200, with a full object model 202 in the application layer supported by object and relational mapping using Object-Relational Mapping (ORM) software. In one embodiment of the system based on Java, persisting Java classes to a relational database is accomplished used a Java Enabled Database Interface (JEDI). JEDI comprises a set of tools to enable Java objects to be persisted as tables in a relational database in a manner friendly to Java. These tools include code parsers, code cleaners, class builders and schema builders.

JEDI was designed especially to solve two problems referred to as the "Collection Add" and "Cache Flush" problems. In the "Collection Add" problem, the ongoing operation of the IHR requires adding elements to persistent collections. Other tools designed to fulfill the function of JEDI tend to load such collections entirely into memory, add elements to them, and re-persist them. As collections grow larger with time, this operation become increasingly inefficient. JEDI is designed to allow elements to be added to collections without loading the entire collection. It does this by maintaining a "partially loaded" collection where some elements may be loaded while others remain only in persistent storage. JEDI maintains a set of operations performed against the collection while in this partially loaded state so that the collection as persisted can eventually be brought up to date.

Like other tools designed to fulfill JEDI's function, JEDI maintains a memory cache of recently used objects. This cache can contain both modified and unmodified objects. At various points in the life-cycle of the cache, it must be flushed to synchronized the persistent storage with it. Other tools, however, can have particularly inefficient caches in that when the cache must be flushed it is not readily known which objects have been modified and a complex process of discovery must be undertaken to determined which objects to flush. As the cache increases in size and frequency of flushing, this process can become extremely onerous. This is referred to as the "Cache Flush" problem. JEDI is designed to know immediately when an object is modified via the natural Java mechanisms and to record this fact in the cache for easy retrieval so that when the cache must be flushed, JEDI never has to engage in a discovery process, but rather, simply refers to the known list of modified objects in the cache.

Part of the persistence layer comprises a content repository 204 provides a storage mechanism for IHR content items, such as binary large objects and other typically non-object oriented data (e.g., images, documents, rule definitions, message templates, information content, and help files), and may comprise standardized technology (e.g., Java). Content attributes or meta data associated with content items may be used for management and selection of discrete content items. Examples of attributes include, but are not limited to, ontology classes, target age, target gender, usage context, effective time, expiration time, keywords, content publisher/manager (used to distinguish between system-provided content as opposed to content authored by a customer or other provider), status and location. The content repository may be viewed as a generic application data "super store," in which virtually any type of content can be handled, and that separates content from data storage technology. If content is received coded according to an external coding system, the content may be applied to appropriate related ontology concepts. Content may be XML exportable and importable. A standard API (such as JSR 170 or JSR 238) may be used to interact with a content repository, thereby providing advantages such as the ability to access other standard content repositories, allow external editing, and transport content between Java content repositories.

Figure 5:
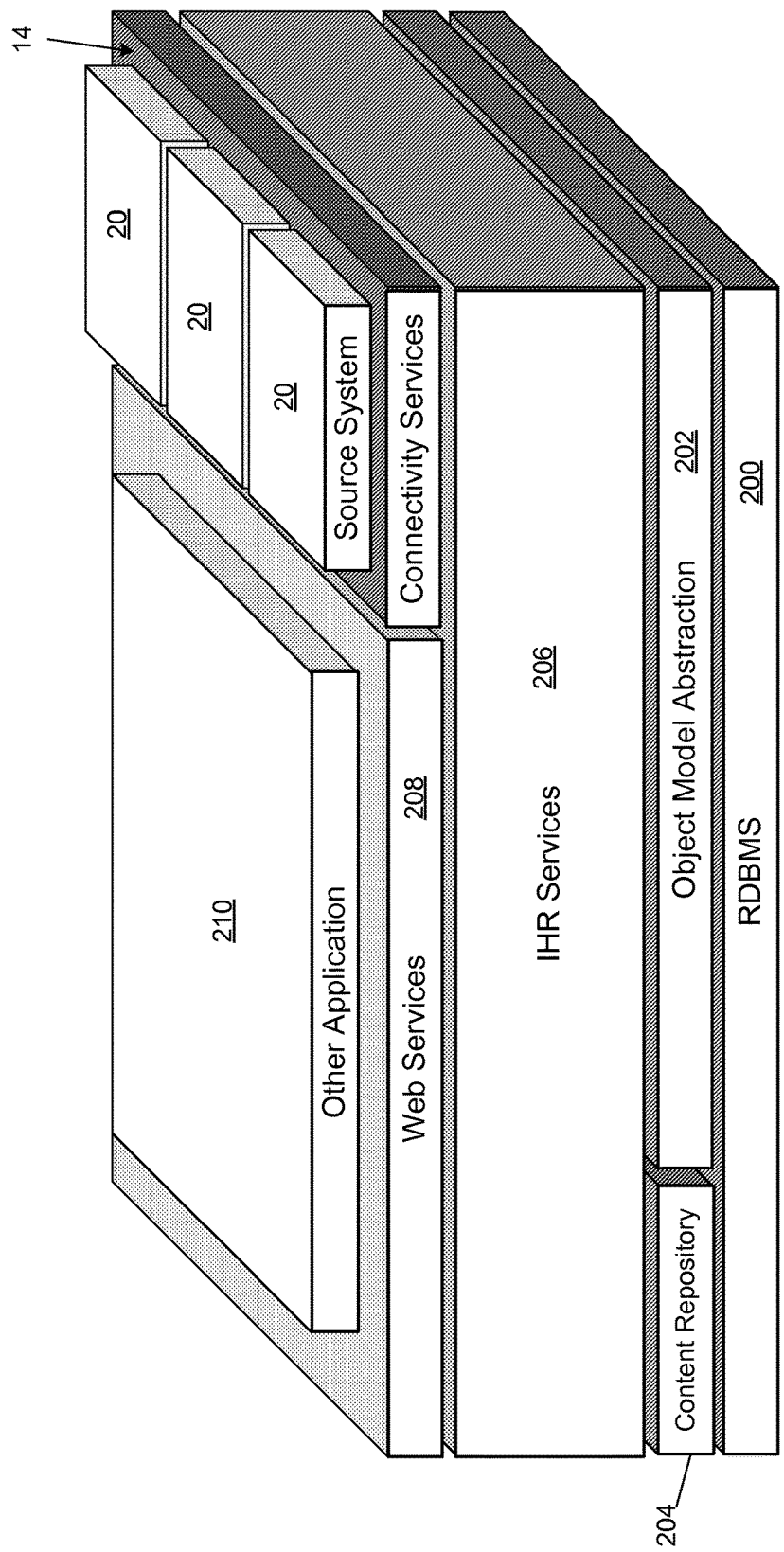
FIG. 5 is another view of an IHR system showing a customized application of an IHR system in accordance with one embodiment of the present invention.

The IHR Services layer 206 provides main IHR capabilities, including but not limited to centrification services, interaction services, custodial services, and system administration services. Connectivity services 14 provide interface means with source systems 20, and handle messages and record parsing. Connection adapters may be used. The web services component 208 provides external access by users to the IHR data and functions through a variety of portlets 32, which may include customer written applications. In one exemplary embodiment, web applications may be instantiated as Java Specification Request 168 (JSR-168) or Web Services for Remote Portlets (WSRP) standard portlets. As seen in FIG. 5, other applications 210 can call web services 208 to create a customized solution.

In one embodiment, each message regardless of source goes through the steps identified herein. Each step in the messaging process contributes to the normalization of source system data. Regardless of source, all data received in the IHR system creates the same data structures (i.e., objects), which are codified and normalization through the same process. The end result thus is healthcare data that is comparable to other data within an individual's IHR (e.g., guideline evaluation, trending and graphing lab results), to guidelines and protocols, and also provides data which is comparable between individuals.

Figure 6:
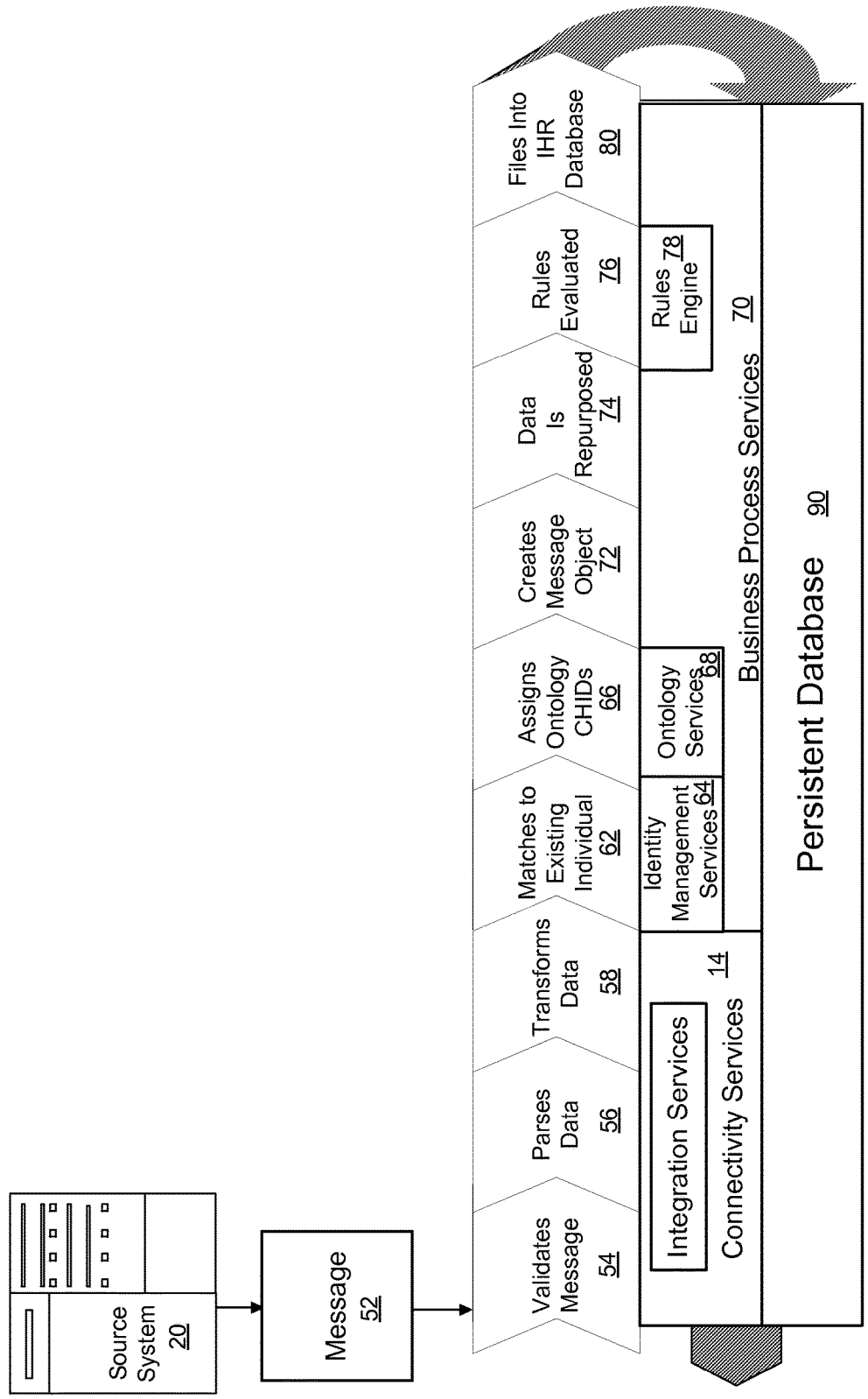
FIG. 6 is a diagram of data flows in accordance with one embodiment of the present invention.
Figure 19:
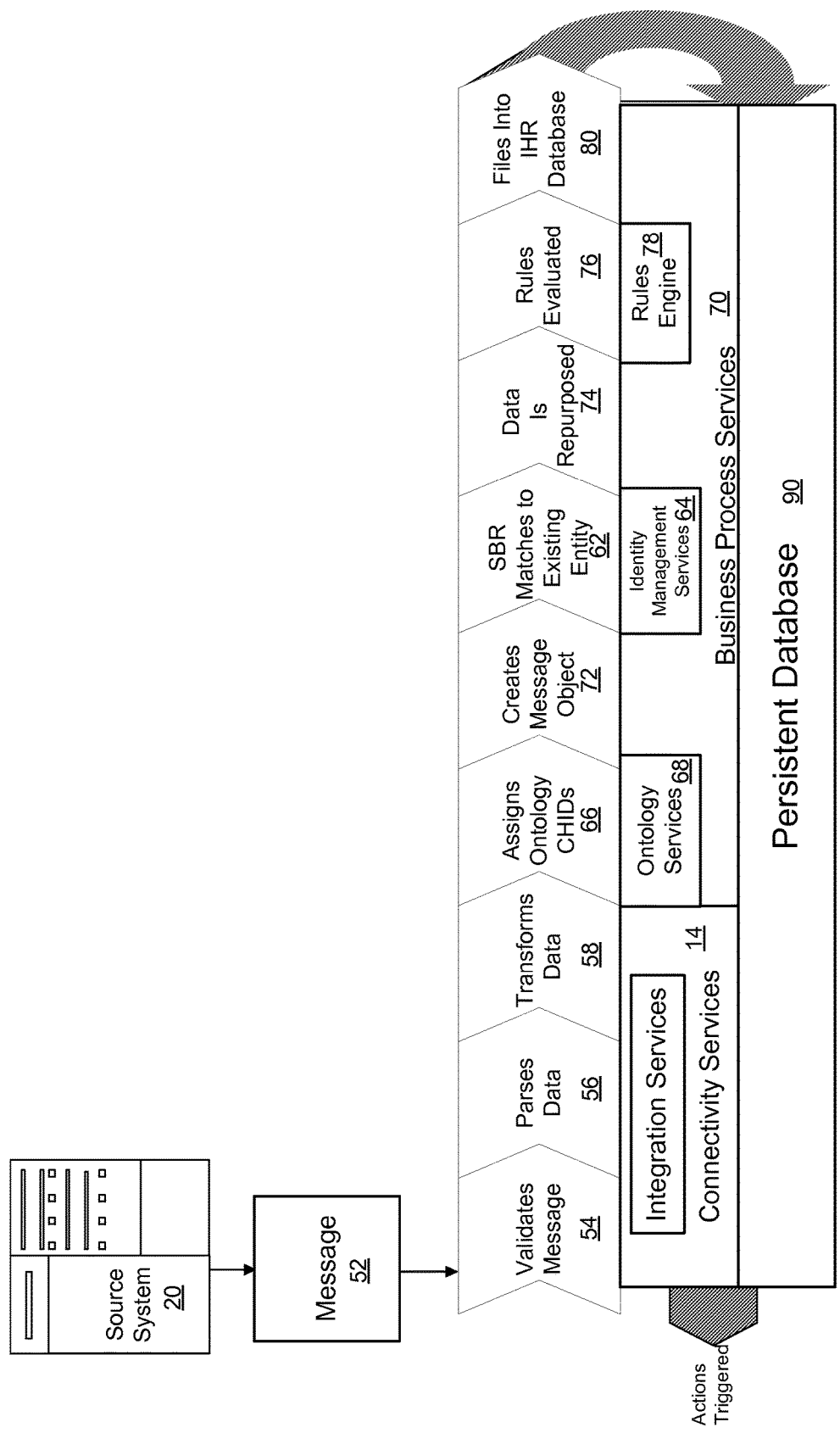
FIG. 19 is a diagram of data flows in accordance with one embodiment of the present invention.

FIGS. 6 and 19 show a general, broad overview of data flows in accordance with exemplary embodiments of the subject invention. Information and data in the form of a "message" 52 (although some other form or terminology is possible) is received from a source 50, validated 54, parsed 56, and transformed 58. These steps are accomplished through integration services as part of the connectivity services 14. The transformed data is then matched 62 to an existing individual through identity management services 64, and assigned an ontology concept code 66 (CHID, discussed below) through ontology services 68. Next, a message object is created 72, the data is repurposed or recontextualized 74, subjected to a rules evaluation 76 using the rules engine 78, and filed 80 in a persistent IHR database 90. Some of these steps may be performed in another order, as shown in FIG. 19. In this embodiment, the identity management services 64, ontology services 68, and rules engine 78 are components of the business process services 70 element of the IHR system. As information from various sources is updated or available, the IHR is dynamically updated on a continuous or periodic basis.

The connectivity services 14 component handles the connections with health data source systems. The connectivity component of the present invention handles both inbound and outbound exchanges in the form of a "message." Connectivity services monitor and manage connectivity runtime components. In one exemplary embodiment, the connectivity services uses an open-source cross-platform HL-7 interface engine, although other platforms may be used. A connectivity configuration manager or connectivity manager stores configuration data, handles channel definitions, and manages the deployment environments. The platform monitors and manages the connectivity runtime components, including the connectivity designer used to define the specific message handling processes, connectivity adapters, and the runtime engine.

In another embodiment, connectivity services comprise a channel-based interface engine for filtering, transforming, queuing and storing messages. The services provide rules-based filtering, transformation and routing. Message types include, but are not limited to, DICOM, EDI, HL-7 v2 and v3, NCPDP, X12 and XML. A variety of connectivity adapters may be used, including, but not limited to, FTP, SFTP, File, HTTP, JMS, LLP, Database, TCP, SOAP and JavaScript. Transformation tools include, but are not limited to, Java, JavaScript, Tcl, Python and XSLT.

Messages inside the system may be stored in a single, common data structure or form. In one embodiment, messages are stored using the CentriHealth Interface Schema (CHIS), which provides a consistent but flexible data structure. This allows for consistent handling of data from multiple source systems.

Figure 7:
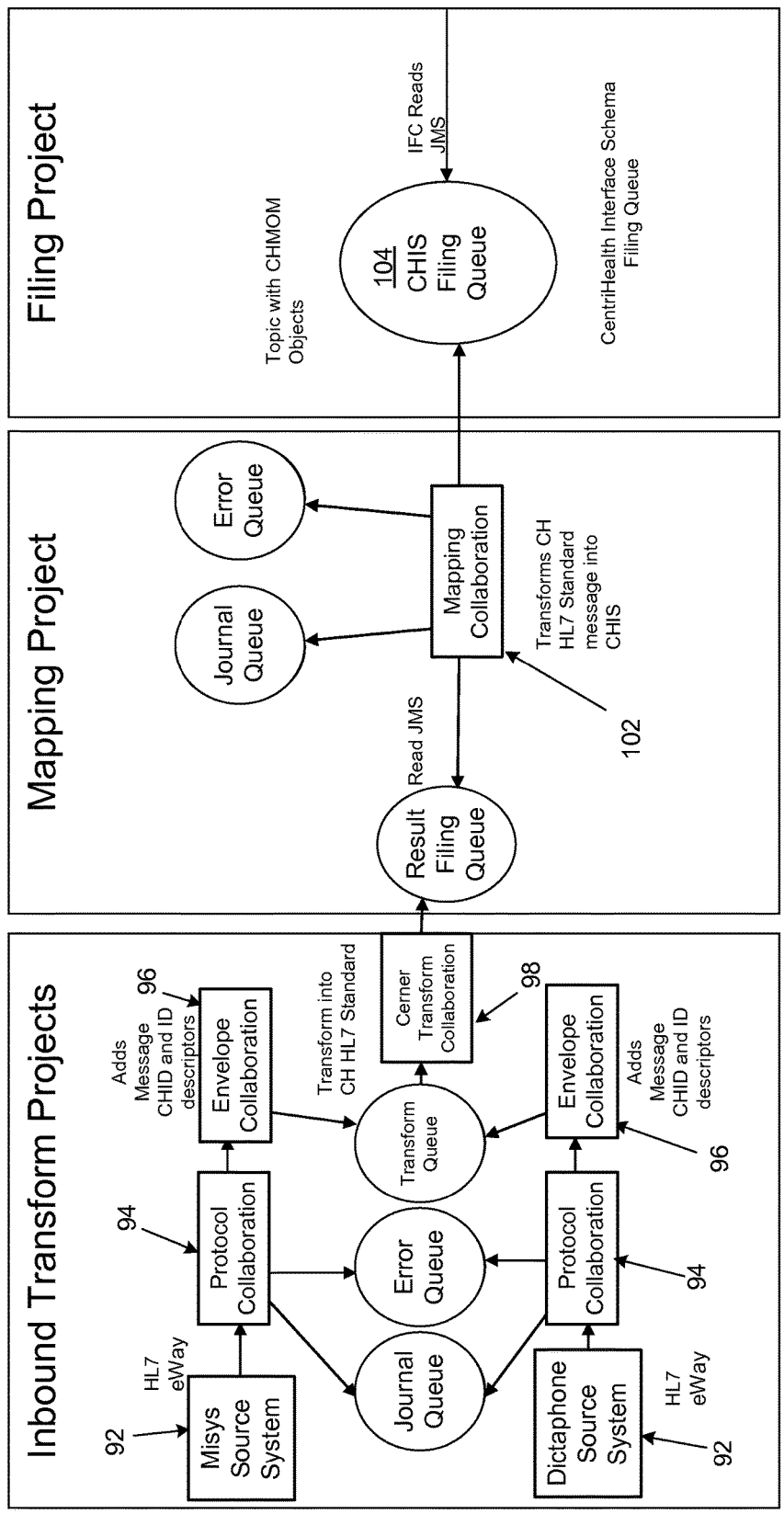
FIG. 7 is a message processing map in accordance with one embodiment of the present invention.
Figure 8:
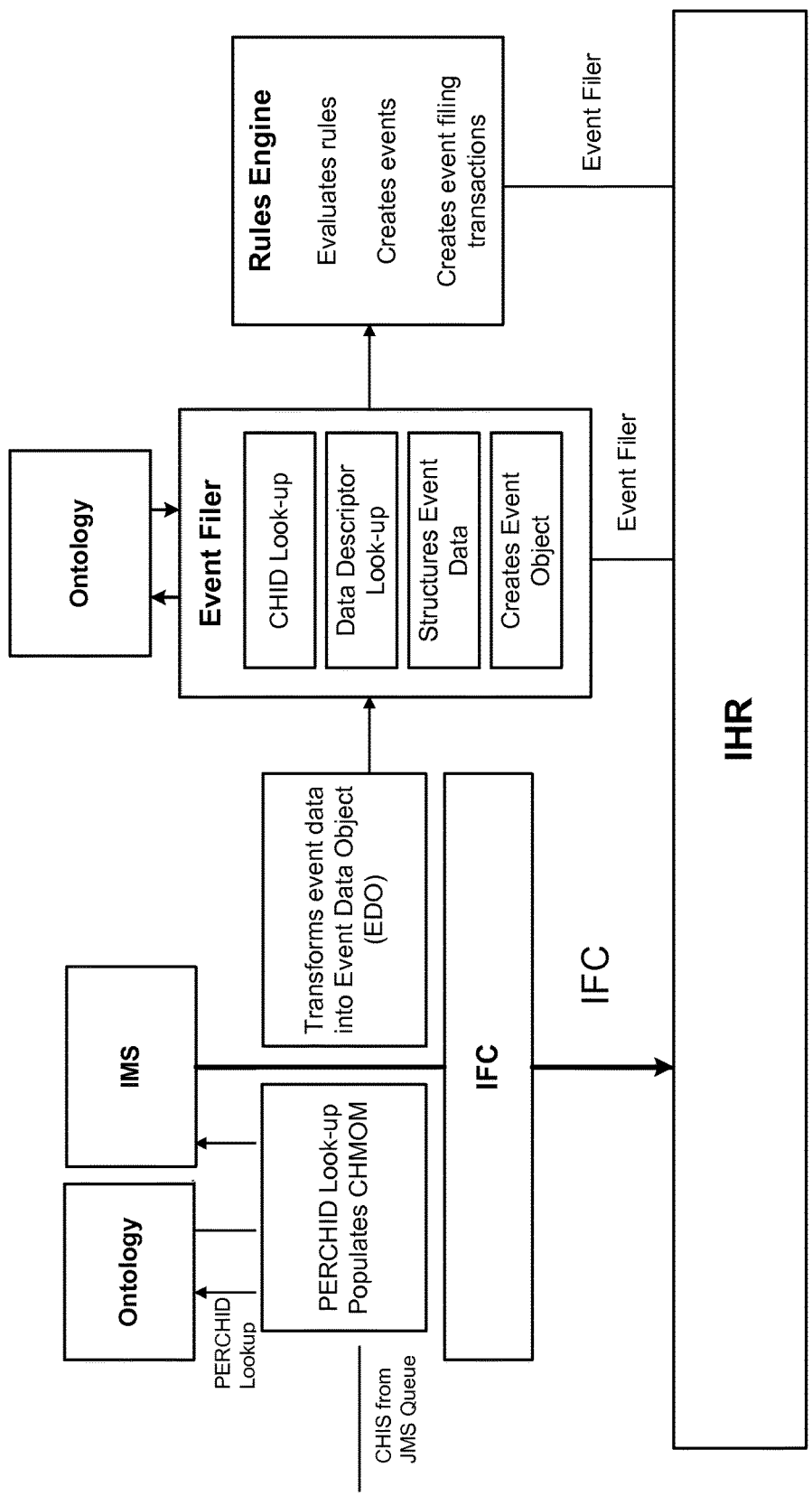
FIG. 8 is a diagram showing interface service processing in accordance with another exemplary embodiment of the present invention.
Figure 20:
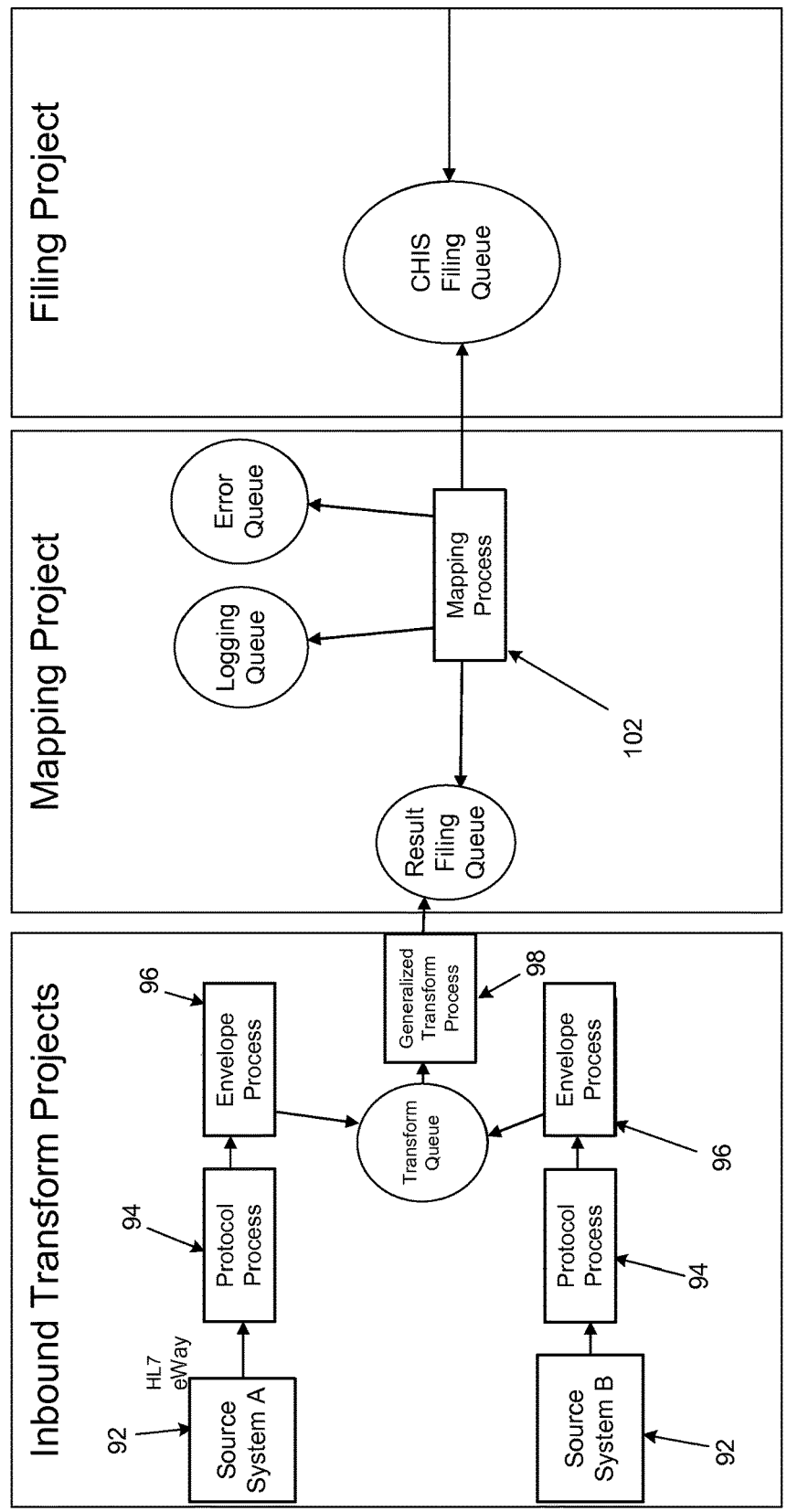
FIG. 20 is a message processing map in accordance with one embodiment of the present invention.

FIGS. 7 and 20 shows the message processing maps for exemplary embodiments of the present invention. Two examples of source systems are shown: in FIG. 20, these are a Source system A 91 and a Source system B 92. The data undergoes protocol 94 and envelope 96 processes, and undergoes transform processing 98. The data is mapped 102 and submitted to the interface schema filing queue 104. Additional interface internal processing is shown in FIG. 8.

Figure 23:
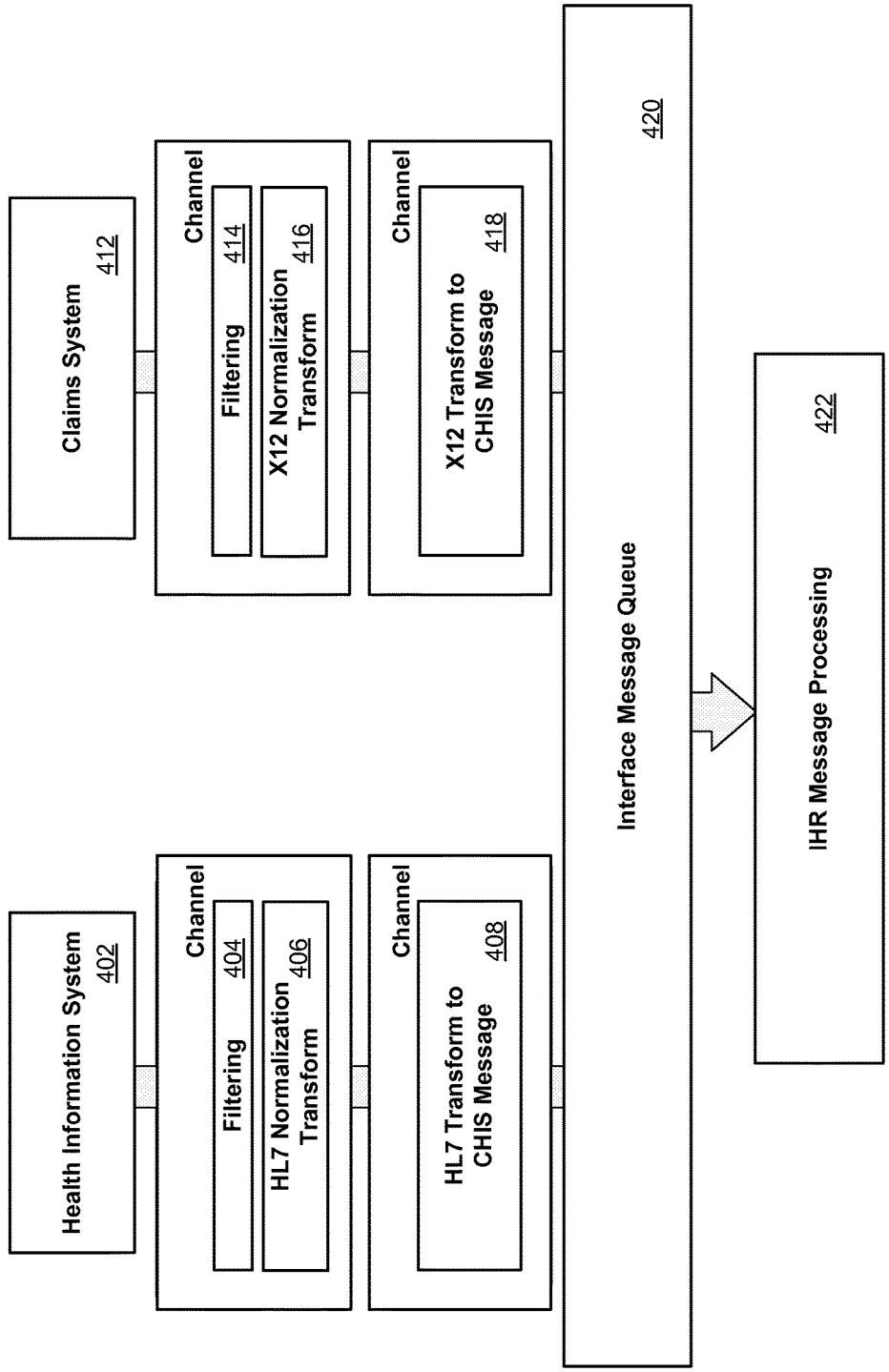
FIG. 23 is a diagram showing message processing.
Figure 24:
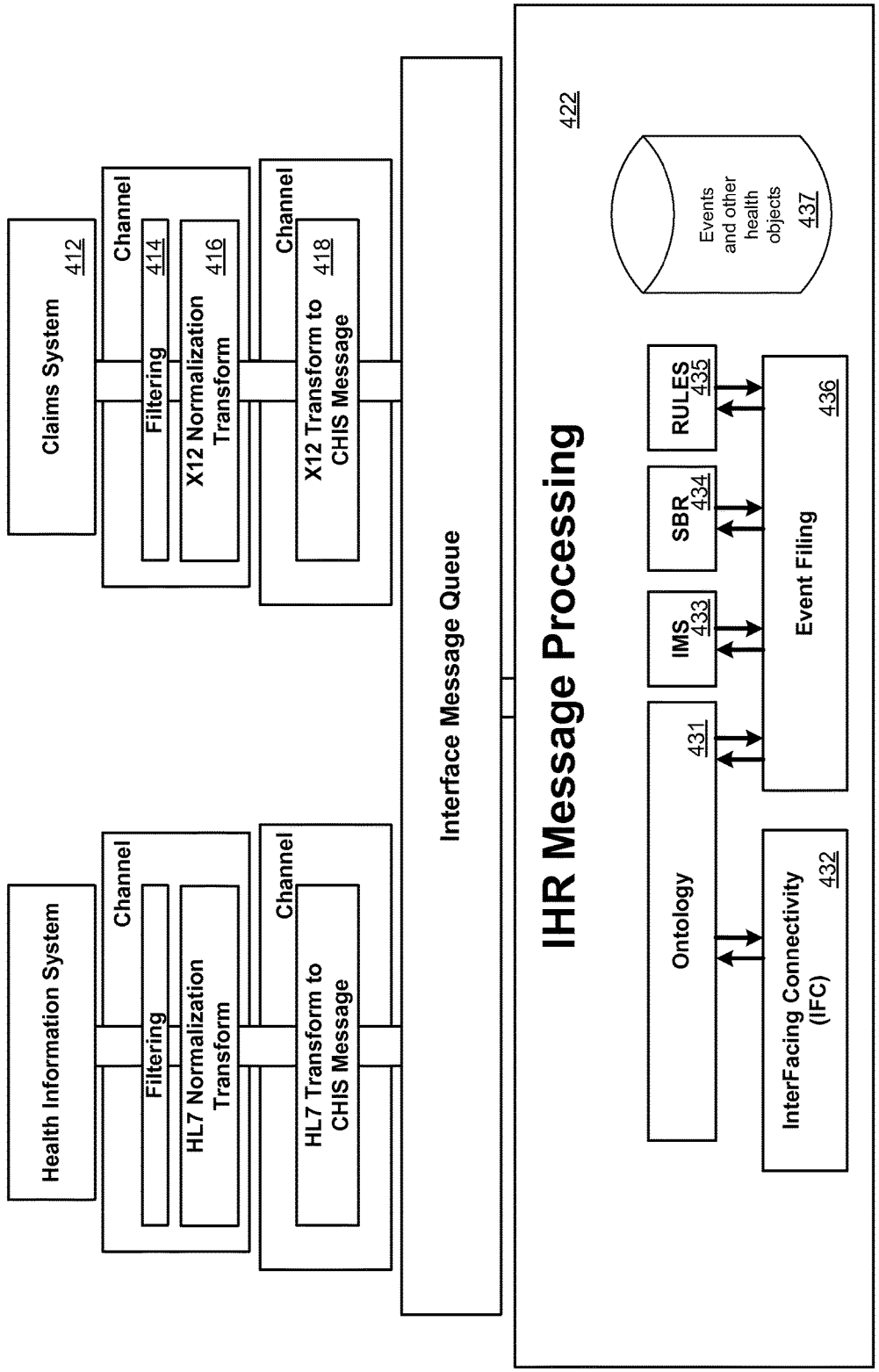
FIG. 24 is a diagram showing message processing and detailed centrification.

FIGS. 23 and 24 show external source message processing (the processing of message data flow from source systems external to the IHR system) for an exemplary embodiment of the present invention. Source systems shown include a health information system 402 and a claims system 412. The message from the health information system is an HL-7 message, and undergoes filtering 404 and normalization 406 before being transformed 408 into a CHIS (CentriHealth Interface Schema) message. These steps include protocol and envelope processes. The data in the message is parsed into discrete fields and is transformed to a system transaction standard based on the message type designated in the source system message. If source system messages are not received in the system transaction standard form, these steps transform the source message received to the system standard. This approach allows an existing data feed to be used to populate the IHR. For example, an HL-7 Result Message currently being generated for exchange between the source system (e.g., Laboratory System) and another system (e.g., EMR System) can be used to populate the IHR with often little to no changes to the message. In the transformation step 408, the standard transaction message is transformed to an IHR-specific, internal representation of the data in the message called a CHIS document. This process begins the normalization of source data into IHR data structures (i.e., objects). The message is then placed into queue 420, and processed 422. The processing queue 420 prioritizes the message for final processing and filing based on various prioritization criteria.

The X12 message from the claims systems 412 is likewise filtered 414, normalized 416, and transformed 418 before being queued 420 for processing 422.

FIG. 24 shows the external system message process with more detail about the processing 422. During the Ontology Process step 431, the data is assigned an ontology concept code through the ontology service (described below and shown in FIG. 21). The system's ontology service functions by reducing each piece of received information to a CentriHealth IDentifier (CHID). This process is another form of data normalization, assuring that the received data is represented by consistent codes which convey the "meaning" of the received data. The ontology is a body of formally represented knowledge comprising a set of concepts, their definitions, and their relationship for a specific domain (in this case, health and healthcare). The ontology is far more than a coding scheme; it not only is a way of representing every concept in health care, but also a way or representing how such concepts interrelate for the purpose of supporting the health care of individuals and the ways in which such concepts can be referenced and invoked.

The InterFacing Connectivity (IFC) process 432 is responsible for creating the IHR data structures (i.e., business objects) based on the data represented in the CHIS document, resulting in the source system data being placed in the appropriate IHR records. During the Identity Matching Process (IMS) step 433, any entity (e.g., persons and providers) data are evaluated used matching criteria to determine whether the entities are already known to the IHR system, and therefore should be added to an existing record or whether a new record should be created. The matching criteria evaluated is specific to the data source (e.g., hospital laboratory system, payor claim adjudication system). Any data in the IHR can be used for matching evaluation. Based on the data provided by a given interface, and the data existing in the IHR, the multi-variable, multi-criteria set matching rules yield a match or no match. When a match is detected, the new information event is filed into the IHR of the person who is the subject of the event (e.g., patient, member, employee). If a match is not found, then a new person record is created and the information event is attached to the newly created personal individual health record. The references to the other persons (e.g., physician, subscriber, guarantor, next of kin) and organization are likewise evaluated using the matching criteria processed the same way: i.e., if match, reference to an existing person or organization; if no match, a new person or organization is created.

The Single Best Record (SBR) process 434 is unique. A SBR is created, comprising each of the key elements that constitute an individual's health record: Conditions; Services; Results; Products; and Care Relationships. Conditions include problems, medical history, family history, allergies, findings (i.e., signs and symptoms) and health status. Health Services includes a timeline list of the healthcare events related to the individual. Health Products include medications, monitoring and assistive devices and medical supplies used. All significant data about an individual's health as needed for their ongoing care is represented as represented by one or more of these elements and more importantly the relationship between them. The SBR comprises a healthcare object containing the "very best" composite information known about a healthcare event, test, or the like.

The Rules Evaluation process 435 occurs before the final step of Event Filing 436. Rules are evaluated every time data is added to the IHR. The normalized source system data is evaluated against rules defined in the IHR system. If the event contains data that matches the triggering criteria defined in a rule, the rule will evaluate. The outcome of a rule is the either the generation of additional IHR data (e.g., Enrollment in a Disease Management group) or an audit entry that indicates that a rule was evaluated but not found to be true. IHR rules are used to update an individual's health status, for health and disease management monitoring, the creation of various alerts and reminders, performance indicator monitoring (e.g., Pay for Performance), and content delivery.

The Event Filing Process 436 comprises the placement of the processed data in the form of an IHR Event and its related health objects into the IHR system's persistent storage or database 437. This process also includes the creation of any additional index files.

Figure 25:
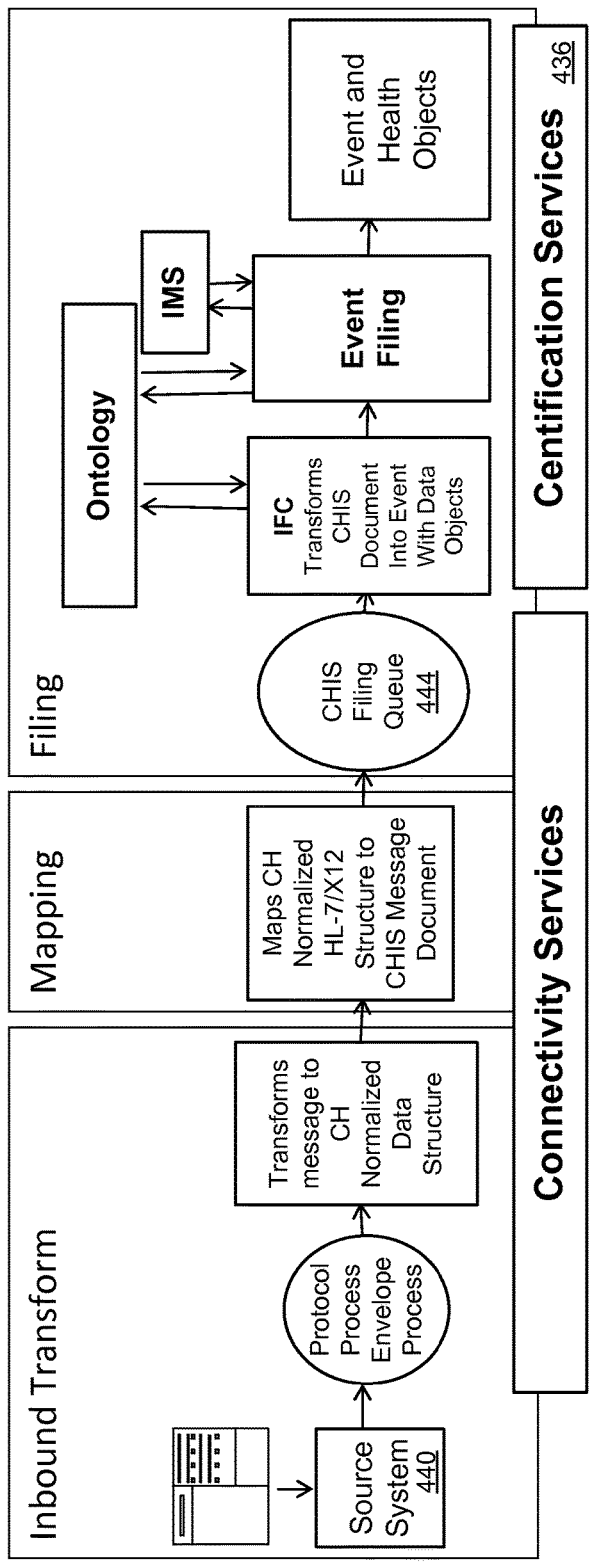
FIG. 25 is a message processing map in accordance with another embodiment of the present invention.

FIG. 25 shows a message processing map for another exemplary embodiment of the present invention. A single source system 440 is shown. The message is normalized and transformed, then placed into the filing queue for subsequent processing by the centrification services component 444.

Figure 26:
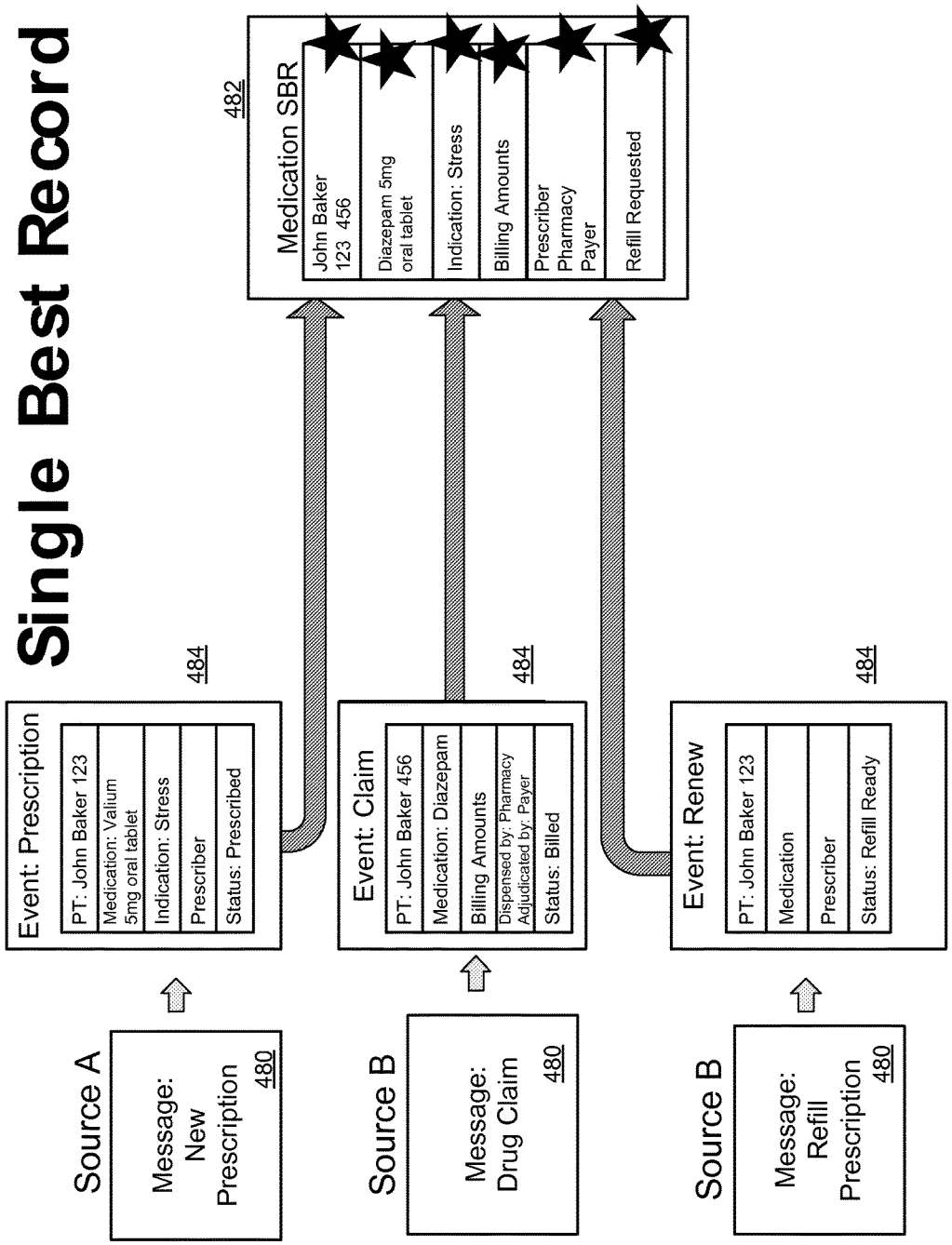
FIG. 26 is a diagram showing creation of a single best record.

In another exemplary embodiment, as seen in FIG. 26, the present invention comprises a Single Best Record (SBR) or a plurality of SBRs. The SBR comprises a healthcare object containing the "very best" composite information known about a healthcare event, test, or the like. In current healthcare electronic records systems and operations, the systems rely on individuals to examine large amounts of information about an individual patient (many instances of this information, in fact, referring to the same event), and then manually determine which portions of which instances should be considered relevant. For example, a mammogram might first be reported via an appointment request, then subsequently by a visit summary when the patient checks in, then a report of the exam several days later, then a claim submissions for payment, then the payment for the exam. In prior art systems, these would be separate records and it would be up to the user to glean the important information from each, even though they all actually refer to the same actual event. The processes of the SBR of the present invention allow all of these records and data sources 480 to be evaluated and properly combined into a single SBR object 482, containing the "very best" information known about the mammogram from all sources.

In short, fragmented partial information about real world health events, received as information events, is reconstituted into a coherent account of those real world events. The SBR object may then be instantiated into the IHR system. Data received at a later time (whether a month, year, or even later) can be subjected to the SBR process upon receipt, contextualized into the appropriate SBR object, and seamlessly made part of the individual's health record.

The SBR process operates by taking each data input as an "information event" 484. Information events do not necessarily have a one-to-one correspondence with real life events. Information events represent the way information about an individual can be received from any source at any time. From each information event, specific subsets of key health data are subjected to the SBR process (i.e., evaluated and combined into the SBR object) to create or update the IHR system's knowledge about a particular individual. This process could include, for example, updating a service, a date, a condition, a product, a test, or the like. Each information event may be compared to existing objects in the IHR system to determine if the information event is describing a new health event or is providing additional information on a known health event and if so whether it is an improvement on what is already known. The SBR process thereby uniquely combines what is learned from external sources with what is already known about that health event or concept to deliver composite information where previously there had only been fragmented data.

In some embodiments, a person SBR may be created, comprising a composite set of the best demographic data the IHR system knows about an entity. Demographic data from each person data object (i.e., each event) is used to update the person SBR.

Figure 28:
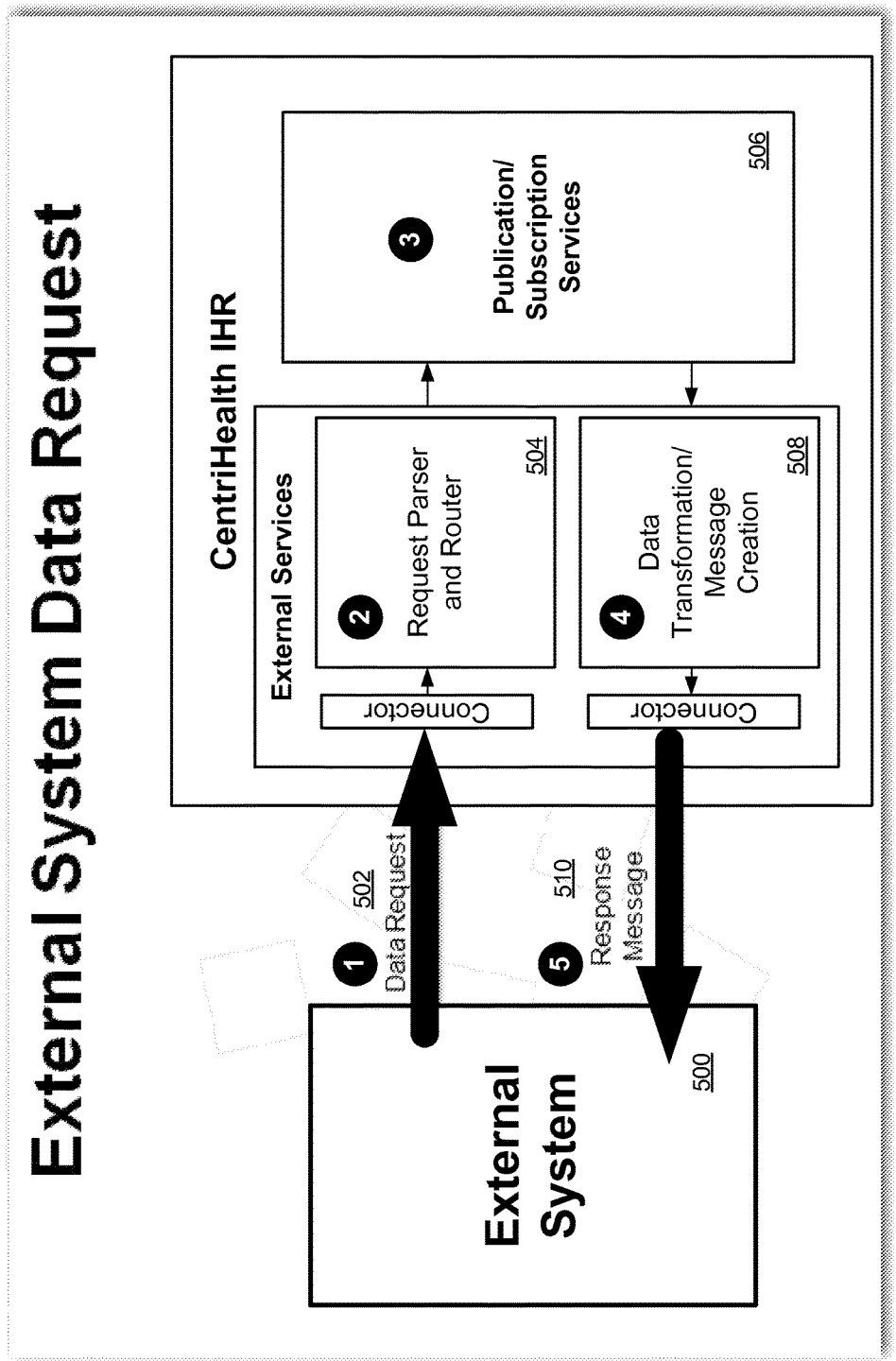
FIG. 28 is a diagram showing the handling of an external system data request.

FIG. 28 shows one example of how the connectivity services of the IHR system handles an external system data request. The IHR appliance uses an open-source cross-platform interface engine as a component of its transformation process. A connectivity configuration manager stores configuration data and manages the deployment environments. The platform monitors and manages the connectivity runtime components, including the connectivity designer used to define the specific message handling processes, connectivity adapters, and the runtime engine. In this example, the external system 500 makes a request for data 502 using a predefined and/or standardized message. The IHR system parses 504 the request message, identifying the target entity or individual and data request type. The request is then routed to the appropriate handler. The Publication/Subscription Services component 506 handles the request, for example, by aggregating the appropriate IHR data specified by the request types. The IHR data is re-coded (e.g., coded to ICD9 from the IHR system internal codes), and transformed 508 to the message format required by the external system. This can be a standard record format (e.g., HL-7) or a custom format determined by the customer or external system. The response message 510 containing the requested data is sent back to the requesting system for processing as appropriate.

Figure 29:
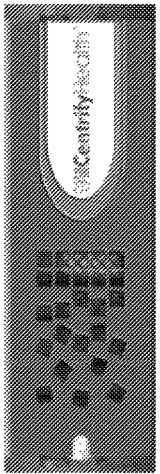
FIG. 29 is a diagram showing the handling of a user request for data via a portlet.
Figure 30:
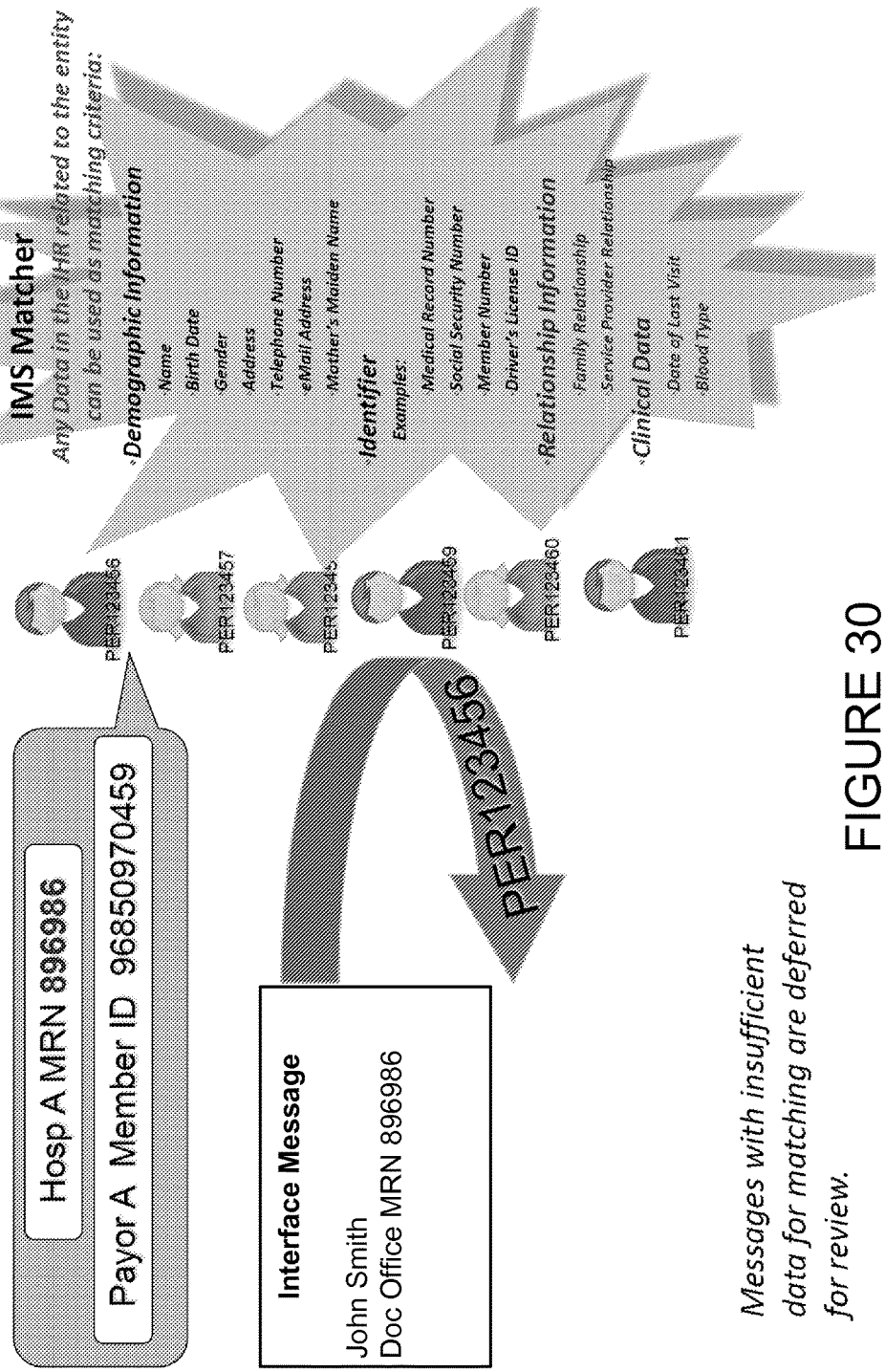
FIG. 30 is a diagram showing criteria matching.

FIG. 29 shows how the IHR device handles a user request for medication data (for example) via a portlet. The user selects the portlet and identifies a patient; the IHR application portlet generates a web service request 550 for the user to access the portlet (e.g., the medication portlet). The IHR system initializes the selected application and checks the credentials of the user, granting access 552 if appropriate. The portlet may prompt the user for identification of the patient if the patient has not already been identified. Upon selection of the patient, the portlet sends a request 554 for the medication list for the patient. The IHR responds with a list of medications requested 556. Sensitive or protected data are either not returned, or returned only with an indication that a protected item exists and if an override of protection is allowed (in the latter case, only certain users may be permitted to override the protection). The user may select a medication item (or items) from the list, which causes the portlet to generate a request for detailed information 558 about the item or items. The IHR system then returns the medication detail 560 requested.

New message types can be easily added. If the "new message" is just a new message to be sent from the external system but within the established transaction standard set, then only a configuration change to indicate that transaction type is now accepted. Transactions are accepted if they have been certified through the system Connectivity Certification process. If there is a new transaction has been added to the standard, then changes are isolated to the following two steps of the messaging process:

Validation and Transaction Standard Transformation— The new message type must be added to the transaction standard, analogous to updating the mapping in an interface engine.

CHIS Transformation—The new message type must be mapped from the system transaction standard to the CHIS, also analogous to updating the mapping in an interface engine.

In one embodiment, the IHR system is dependent on the ability to accurately identify or create an entity, and link data correctly. Identity management services (IMS) 62 handle these functions. In an exemplary embodiment, two types of entities are of particular importance: persons (including, but not limited to, patients, members, consumers, clinicians, and individuals), and organizations (including, but not limited to, employers, payors, and providers, such as hospitals, reference labs, imaging centers, or nursing homes). IMS functions include creation, matching, merging, and unmerging for each type of entity.

One goal of identity matching is to have the disparate data about an entity from multiple source be placed in or inserted into a single record (e.g., the SBR). The persons and/or organizations within a message or input data are matched to the persons and organizations known to the IHR system (or creates a new record for the entity if none previously exists). The identity matching process returns a CHID that has been assigned to the entity. Alternatively, criteria matching can be used to effect a match. Criteria may comprise demographic information (e.g., name, birth date, gender, address, telephone number, email address, mother's maiden name), identifiers (e.g., medical record number, social security number, member number, provider ID, driver's license ID), or relationship information (e.g., family data, service provider relationship). Probablilistic matching may also be used.

For criteria based matching, in one exemplary embodiment, a library or table of matching criteria rules may be used. Rules may exist for person matching, or organization matching. Each rule may comprise one or more criteria which must be met to achieve a successful match. Rules may be electronic system specific. As best practices are established, they may be applied to other electronic systems.

If the system determines that no match exists, then the system may create a new entity record.

In one exemplary embodiment, all demographic source data is treated like any other data object; any demographic source data received in a message, form or web service input will create an event. This permits the system to display the demographic date in the relevant event, and be able to "rematch" the person and/or re-SBR as needed.

Figure 9:
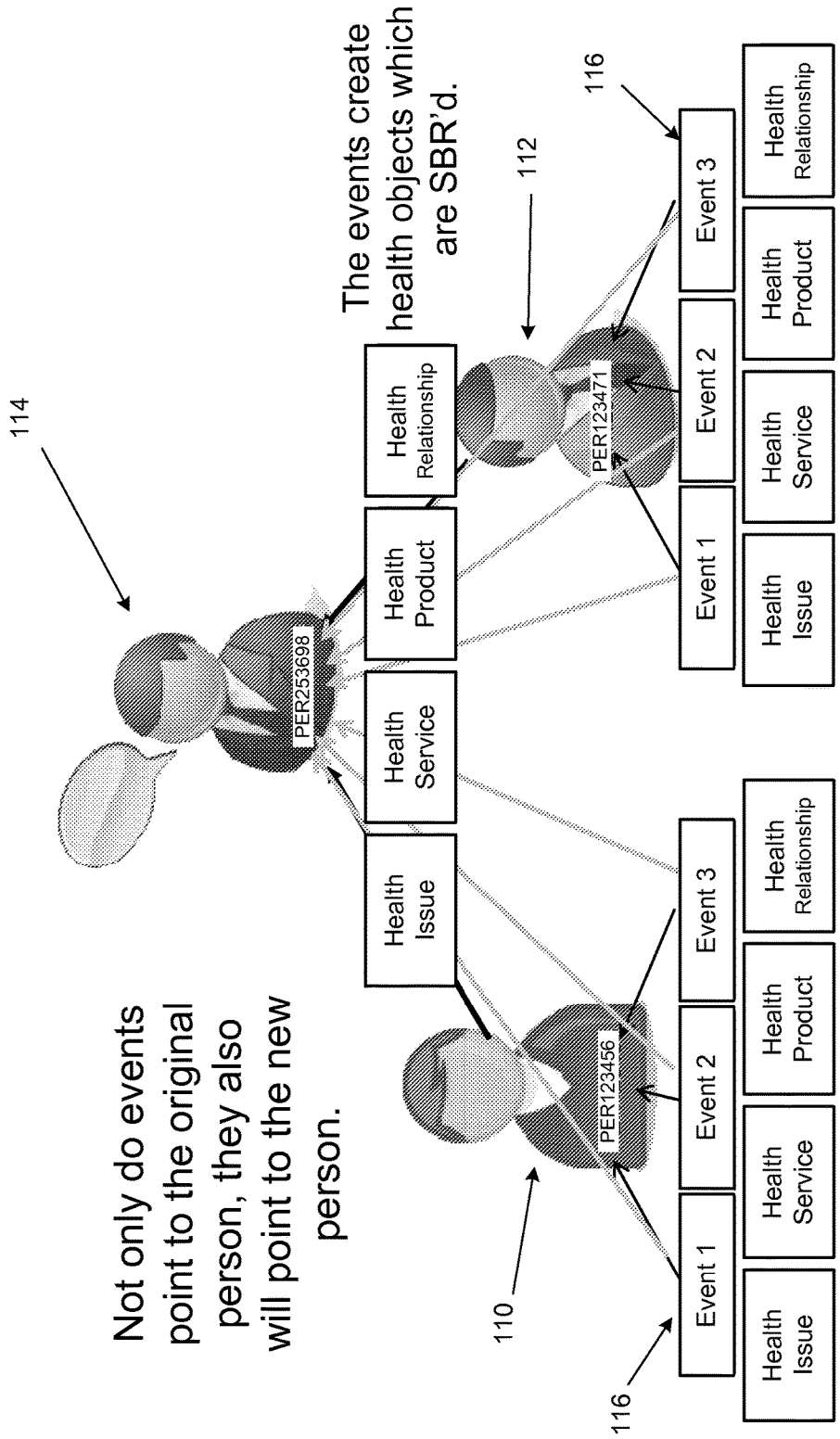
FIG. 9 is a diagram showing merger of entities in accordance with an exemplary embodiment of the present invention.

In another embodiment, when two entities 110, 112 are recognized by the system to be the same entity, they are effectively merged by creating a third entity 114, as shown in FIG. 9. The data and events from the two entities are merged. Not only do events 116 point to the original entity, but they also point to the new entity. New events need to be attached properly: new data is attached to the most specific (lowest level) entity, as well as higher level entities. Any new data generated directly by or on the merged entity will be attached to that entity. Merged entities may themselves be merged.

Conversely, entities may be unmerged (i.e., linked entities are separated). Audit histories may be created for each entity involved in the unmerged, and formerly merged entities can be accessed through the audit history. In the unmerging process, any events on the merged entity must be manually assigned to the appropriate lower level entity.

In another embodiment, identity matching may follow the same process as the SBR process, as seen in FIG. 25. That is, the process determines whether a new data item is already known to the IHR (i.e., part of a known object), and if not, creates a new SBR object. Each object has its own "matching" subject to the SBR rules. For the case of identity matching, the IMS matching rules now would be the SBR rules. The iterative SBR process results in better matching. Identity matching also may be performed on organizations as well.

In yet another exemplary embodiment, the present system comprises a unique health ontology to overcome limitations of the prior art in representing knowledge and information. A uniform and unifying way of dealing with health information is highly desirable. Most prior art systems contain some type of coding scheme, internal or external. Some of the more popular schemes include the Standardized Nomenclature of Medicine (SNOMED), and ICD-9 or ICD-10 (the International Classification of Disease, including the clinical modification variations). While these coding schemes have long been proposed as needed for health IT systems, and have been adopted and used by many systems, they have been used primarily in retrospective studies, and have not had the desired impact on real-time health delivery.

Ontology is a body of formally represented knowledge comprising a set of concepts, their definitions, and their relationship for a specific domain (in this case, health and healthcare). The ontology of the present system is far more than a coding scheme; it not only is a way of representing every concept in health care, but also a way or representing how such concepts interrelate for the purpose of supporting the health care of individuals and the ways in which such concepts can be referenced and invoked.

In one exemplary embodiment, the system's ontology services function by reducing each piece of received information to a centrified health identifier (CHID). Each CHID has both relationship and attribute information, allowing it to know far more about the meaning of that isolated piece of information in relation to the individual than just the information received. For example, a C-section is not just a surgical procedure. There are a number of "knowledge concepts" that can be inferred by virtue of the fact that a patient has had a C-section. The various health care coding schemes that are available with regard to any particular patient may relate not only to the C-section but, perhaps, to other findings related to a C-section. These interrelationships are represented in the ontology, so that the universe of issues and findings to be associated with such a patient becomes part of the inherent knowledge used and conveyed by the subject invention. For instance, if it is known that an individual has a C-section, the ontology also informs the system that the individual is a female, has been pregnant (gravida>0), and has had a non-vaginal delivery of a fetus or a child, among other things. As another example, the structure and content of the ontology means that an elevated Hemoglobin A1C informs not only that the person has diabetes, but also the inheritance of an entire class of characteristics of people that have diabetes.

The ontology is "full of" attributes that identify characteristics of a given concept, including but not limited to how it is displayed, where it is displayed, and what privacy and confidentiality treatments apply. Data may be stored both as original source vocabulary code, and as IHR concept code (e.g., CHID).

In one exemplary embodiment, the ontology of the present invention comprises over 1,500,000 source vocabulary terms, referencing over 300,000 distinct concepts represented as CHIDs. There are a large plurality of linkages among the CHIDs and the concepts that can become more mature and meaningful as additional use cases are examined and incorporated into the system. Concepts can be mapped bidirectionally to and from various source vocabularies. This representation of information allows operations not possible in the prior art. As a nonlimiting example, patients and caregivers can have the benefit of the effective application of rules-based care algorithms (such as are putatively applied by disease management companies) in real time, as opposed to the delayed, after-the-fact interventions that are usually applied by quality monitoring and disease management companies.

In another exemplary embodiment, ontology web services identify and deliver the appropriate concept from the IHR system ontology. Examples of methods used by ontology web services include getCHID (used when a foreign key is passed in order to retrieve a mapped CHID), getForeignKey (used when a CHID is passed in order to retrieve a mapped foreign concept ID), getName (used to retrieve a system controlled medical vocabulary concept term), and getForeign (used to retrieve a foreign vocabulary concept term).

In one exemplary embodiment, the Java code has awareness of and operates with the following code sets: HL-7, X12, ICD-9 CM Diagnosis, ICD-9 CM Procedure, ICD-10 CM Diagnosis, CPT4, LOINC, RxNorm, SNOMED CT, HCPCS, HL-7 v3, HL-ICDA, NDC, FDB, RVU, NCPDP, ISO Standards, DRG, UB92, NAICS, SIC, LCA, FAHCA, UNS, CDT, DRG F8, Medispan Drug, Medispan Condition, Medispan Allergen, Medispan Alert, Medispan Form, Medispan Route, Medispan Unit, AMA, ACR, CVX Vaccine, SSL, and Rx Hub.

In various exemplary embodiments, the use of the ontology to cross all sources, uses, and users of data to provide an individual-centric view and to support the determination of the proper single best record is unique.

Figure 10:
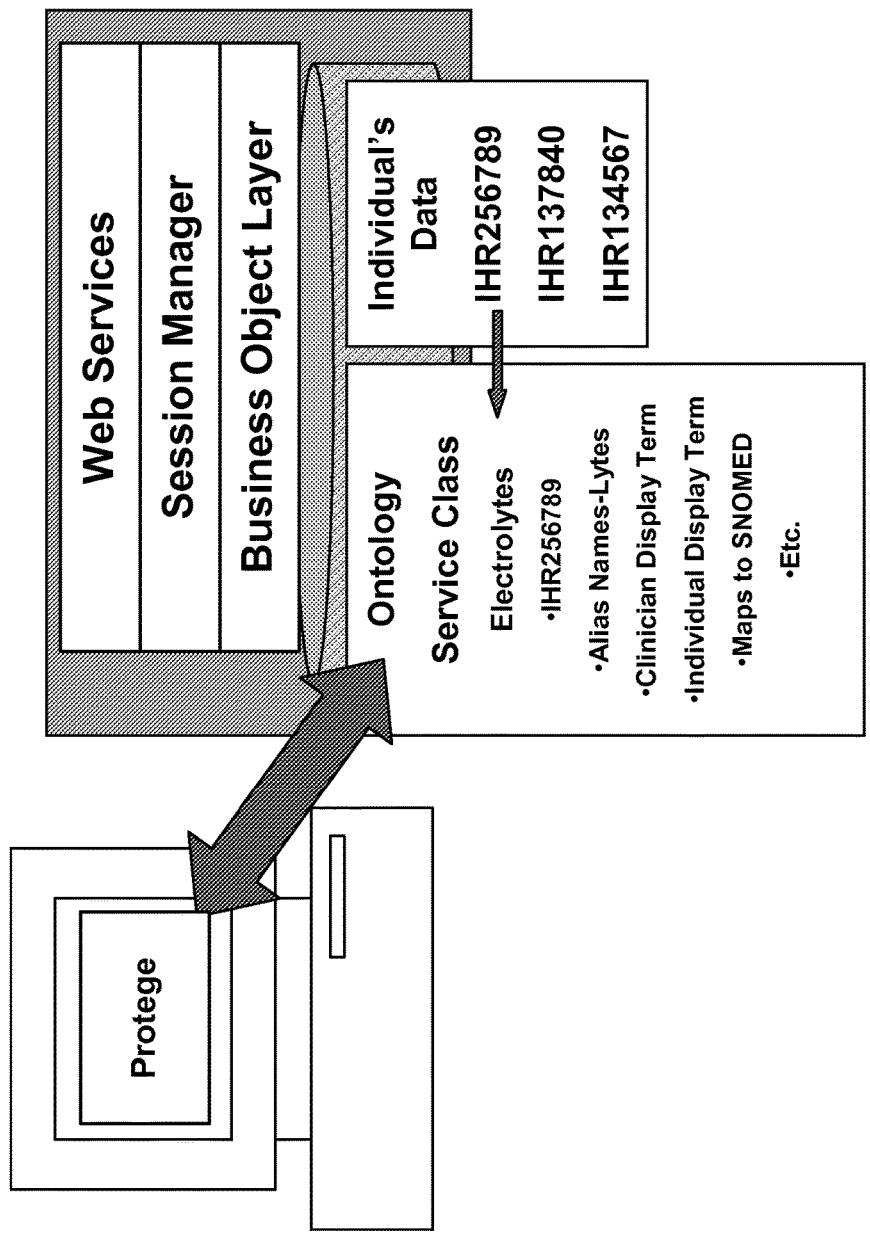
FIG. 10 is a diagram showing the relationship of the ontology tool to the IHR database in accordance with an exemplary embodiment of the present invention.
Figure 21:
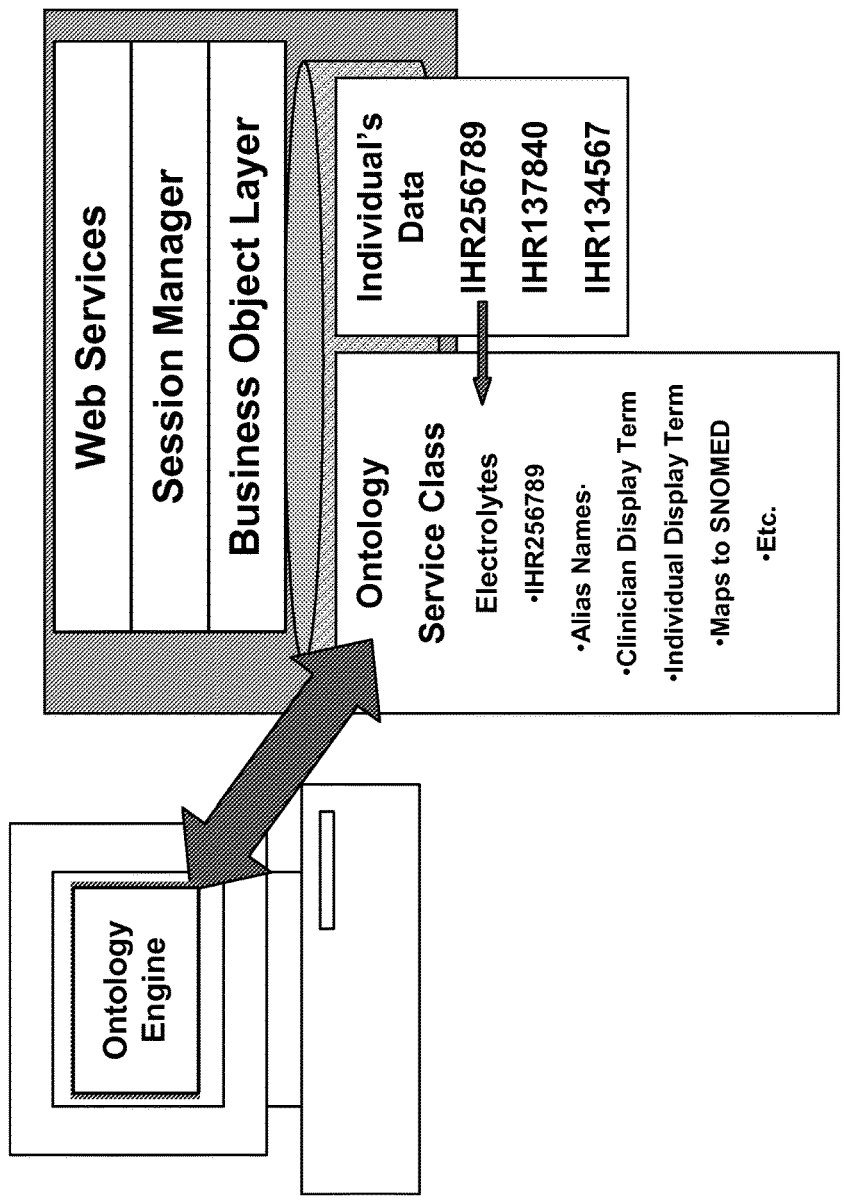
FIG. 21 is a diagram showing the relationship of the ontology tool to the IHR database in accordance with an exemplary embodiment of the present invention.
Figure 22:
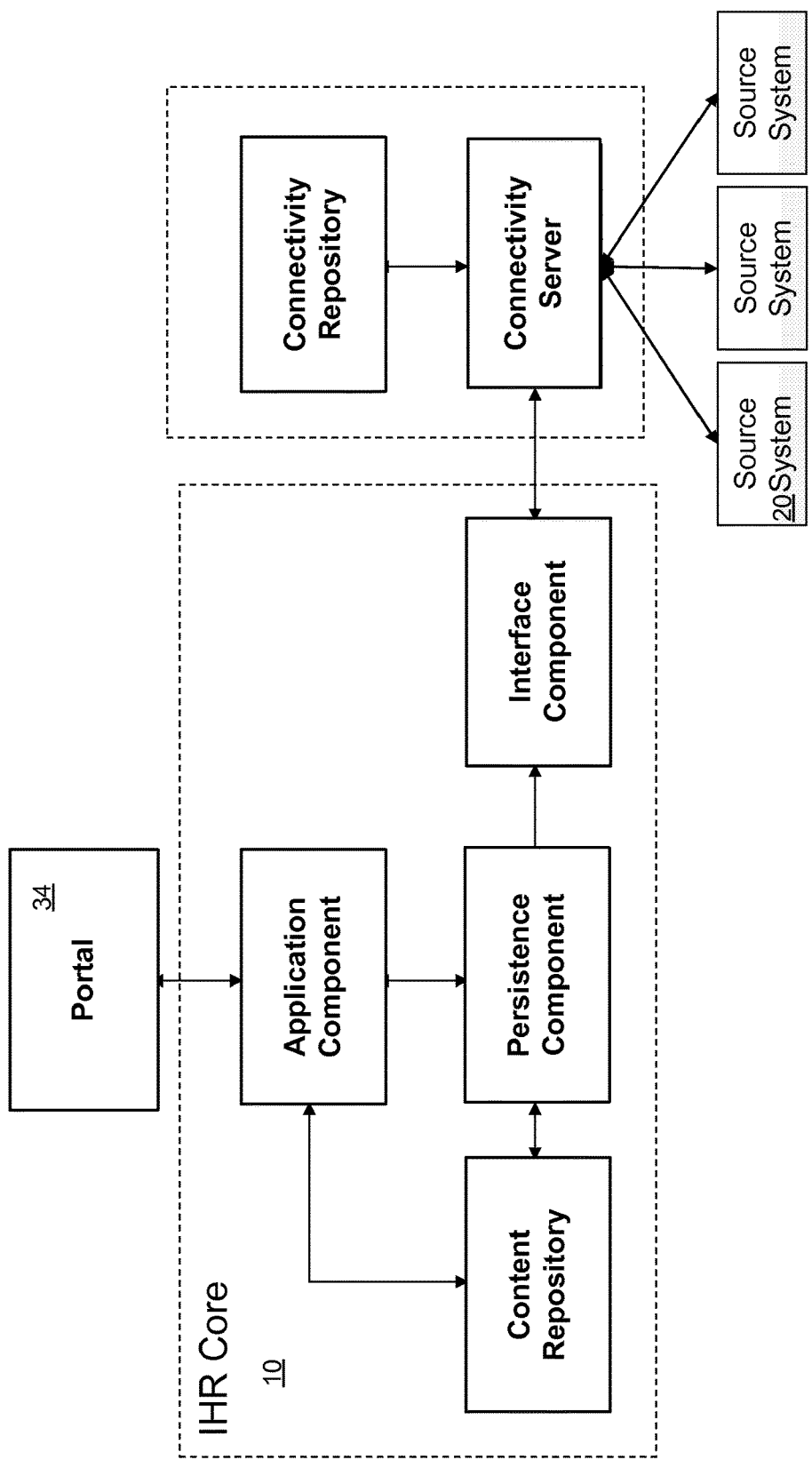
FIG. 22 is a diagram showing elements of an appliance in accordance with an exemplary embodiment of the present invention.

Another goal of the ontology is to enable data in the IHR system to "interoperate" using rules that create alerts and reminders, update the individual's health status, monitor health action progress, and similar activities. To achieve this, the data in the IHR system must be coded, have context and meaning, be linked to content, and be comparable (as seen in FIGS. 10 and 21). Benefits gained from this system are improved interoperability, increased user adoption, better clinical decision-making, reduction of medical errors, improved data mining, and the support of better outcomes analysis, among others.

Source vocabularies include a number of code systems and sets. These include, but are not limited to, the following: ANSI X.12 (standard for defining electronic data exchange of healthcare administrative transactions); ANSI HL-7 versions 2 and 3 (standards for the exchange, management and integration of electronic healthcare information); CPT (Current Procedural Terminology); HCPCS (Healthcare Common Procedure Coding System); ICD-9-CM and ICD-10 (International Classification of Diseases and Procedures); ISO (Internal Standards Organization); LOINC (Logical Observation Identifiers, Names and Codes); NACIS (Northern American Industry Classification System); NCPDP (script ePrescribing standard); NDC (National Drug Codes); NUBC (National Uniform Billing Code); RxNom (nomenclature for clinical drugs); and SNOMED CT (Systematized Nomenclature of Medicine). Proprietary code sets from source systems may also be used as needed.

In one exemplary embodiment, a central ontology may be maintained and updated on a continuing basis by a service provider. When significant changes are made, the updated ontology is released. Custodians and health advocates may be able to make local extensions to their ontology.

In another exemplary embodiment, the system comprises a connectivity application module that supports the IHR system approach of taking data from any authenticated source at any time. The connectivity application module receives, understands, and processes data, information and messages regardless of the type, allowing almost any type or kind of source to provide information to the IHR system. In one exemplary embodiment, information from over 150 sourcing systems can be incorporated in a particular installation of the IHR system. The number of sourcing systems is unlimited.

In yet another embodiment of the IHR system, the presence of understandable and understood data in the system provides the opportunity to patients, caregivers, and other users to actually use the data for a wide variety of uses and applications. Such uses include, but are not limited to, quality enhancement (e.g., duplicate blocking, interaction detection and resolution, real-time adherence to disease management and other protocols, and best practices enforcement), and efficacy/efficiency optimization. Many of these uses and applications may be accomplished through a rules detection and execution environment, which may be seamlessly incorporated into the IHR system to provide a heretofore unavailable level of rules integration.

The IHR rules environment follows the objects created for the system using fully ontologized data. Rules can be evaluated in real-time as IHR data is created or modified (e.g., data received from another system in a message; data entered or changed by user; data created by the centrification process), at a scheduled time (note that a system task object can schedule itself at specific times or frequencies), or on demand (e.g., invoked by a rule runner portlet, or by injection of a message). Thus, each time an object is created or modified, all applicable rules are evaluated to see if particular criteria are met. The process includes, but is not limited to, the updating of all status indicators, and the sourcing and scheduling of rules involving time-dependent criteria (e.g., one mammogram per year for females over 40). Accordingly, in one exemplary embodiment, with every data creation or modification event, and with every tick of the clock, the potential exists for rules to execute. Rules also can trigger other rules, supporting the complexity of the health delivery system as it actually works.

The IHR system uses rules in a variety of ways, as seen in FIG. 31. An example of rule categories is shown in FIG.

32. Possible rule types are shown in FIGS. 33-37. An example of a rule creation process is shown in FIG. 38.

An individual's health status indicators thus may be as up-to-date as the data received into the IHR system. Whenever new data is added to an individual's IHR (or data is modified), rules are evaluated. A rule scheduler may also be used and an object may schedule itself at specific frequencies. The scheduler executes rules evaluation for time-dependent criteria. This may include age-dependent rules. Kick-off notifications may be given at appropriate times prior to health action due dates as well.

Figure 39:
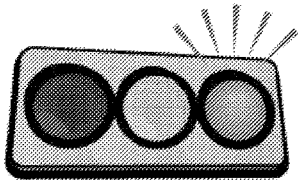
FIG. 39 is a screen shot of a personalized content action plan update.

In general terms, the IHR system may use rules to categorize individuals and users, update and notify users of the individual's health status, generate health maintenance actions, process action plans, create data from other data, perform data entry business logic, protective monitoring, data entry edit checks, select appropriate CHIDs, the flow of applications, support subscription-publication services, and present personalized content. When a rule is true, an action may be triggered. Nonlimiting examples of rule applications and actions may include the following: create content; display content; create lists; create health issue objects; create health services objects; create a health calendar entry; update status; update an action plan (see FIG. 39); create an external system message, trigger a secure message; trigger a reminder; invoke a content display; list an entry; send a message to an external system; send a fax; supplement a list; complete a system task; and add to the health calendar.

In one exemplary embodiment, business rules are managed independently of application code changes. Non-programmers may be provided with the ability to create and change rules. This ability may be provided through add-on decision table support. Multiple rule types may be supported, and an audit trail of rule changes may be maintained. The system may receive inbound messages for rules executed on an external system.

Decision tables may be used to represent conditional logic. Spreadsheet programs may be used to set up rules. Rule creators can define parameters while scripts that map the rule data to the underlying object model are hidden.

In one exemplary embodiment, rules are cascading, such that a rule can be triggered by another rule. A succession of non-recursive and recursive rules can trigger each. Rules are generally intended to accomplish a particular discrete transformation of the IHR data. This new state, may, in turn, specify that additional rules be run. These rules may be the same as or in addition to the original rules, but each of which, in turn, accomplishes a transformation of the data. This process, referred to as a cascade, is allowed to proceed organically until data transformation no longer specifies any rules to be run.

Another embodiment comprises a rule population approach in which individuals are included or excluded from a particular group or population, such as a disease, wellness or preventative health group. Rules are executed on the members of the group. Thus, for a particular individual or group member, the rules are executed until the individual is no longer in the group, or until a clinician has indicated that a particular rule or criterion does not apply to the specific individual.

Population is one of the cases of rule cascades and constitutes one of the preconditions which may signal rules to be run. When an individual is added to a particular population, that signals certain rules relating to that population to be applied to that individual as part of the rules cascade. Similarly, when an individual is removed from a population, additional rules may be added to the cascade. In general, it should be noted that individuals usually are not directly added or removed from particular populations, but their data state indicates their membership in certain populations.

Another exemplary embodiment of the present invention comprises a repurposing or recontextualizing object program (ROP). The ROP overcomes a fundamental limitation of many prior systems where the early delineation of what each data item is for, and why, forever pigeonholes each data element received. In the IHR system, the data received by the system can be used for a variety of purposes, many originally contemplated when the system was assembled. The ROP, in conjunction with the above features, results in a system allowing repurposing or recontextualizing of the data.

Figure 27:
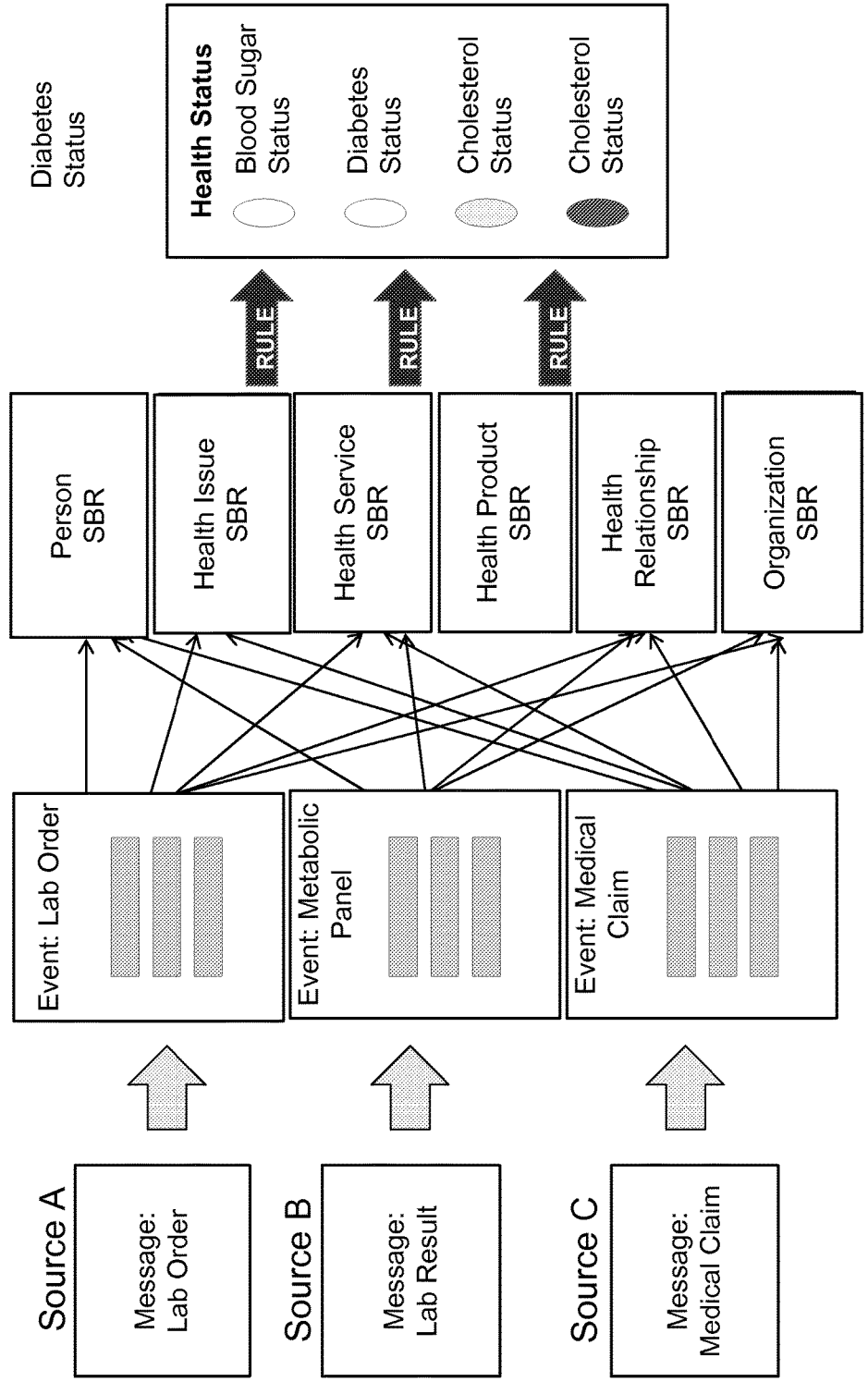
FIG. 27 is a diagram showing the centrification process.

The combination of the above processes and components results in a process known as centrification. As seen in FIG. 27, the centrification process takes fragmented, poorly formatted, and often incomprehensible health care data, and turns it into useful, individual-centric health care information.

In one exemplary embodiment, the conceptualization, design, development, and implementation processes that have resulted in the ontology with specific reference to health care, have been generalized and applied throughout the entire system. Some or all of the application constructs (such as, but not limited to, the display and rendering models, labels, input fields, and content managers) are codified, allowing them to be controlled non-programmatically.

In yet another embodiment, the IHR system uses a metadata content control model which allows content from a plurality of streams and sources to be matched, displayed, and linked with appropriate keys provided through the ontology or other IHR system services. This provides a level of personalization with regard to content display to both individual and professional users that is not present in the prior art.

In another embodiment, the IHR system determines a confidence indicator that indicates how "good" an entry in the IHR system is based on a variety of factors. Factors include, but are not limited to, the source, how much processing was required, and derivation history. In one embodiment, confidence is based on the following information: data source, identification reliability (e.g., was a SSN used? an MRN?, only a name?), derivation, and certainty of derivation. Identification reliability can vary between source systems (e.g., MRN may be more reliable from one source than another). Derivation can propagate and elevate uncertainty. Calculation of confidence can take into account aggregation of uncertainty.

In one exemplary embodiment, calculation of confidence proceeds as follows:

1. If the data in question is received directly from a source system, then its confidence is a factor of the confidence in the source, combined with the certainty of identification of the data target. Statistically, this is multiplicative—if one has an 80% confidence in the data source and a 90% confidence in the identification of the data target, then the confidence of the data should be 80%*90% or 72%. In one embodiment, the assignment of confidence to a particular data source is initially arbitrary based on characteristics attributed to such data source, but is adjusted over time based on the observed quality of data received from such source. In yet another embodiment, it is possible to assign a more definitive confidence to the identification of the data target base on known matching algorithms.

2. If the data is derived data, then the confidence is the aggregate confidence of the source data combined with the confidence of the derivation. A simple example would be that one piece of data directly implies another piece of data with absolute certainty. In this case, the confidence of the derived data is identical to the confidence of the source data. In another case, it might be that a particular piece of data implies another piece of data 95% of the time. In this case, the certainty of the derived data would be 95% of that of the original data. Finally, if a piece of data is derived from two or more pieces of data, then its confidence is the statistical aggregate of the confidences of its source multiplied by the confidence of its derivation: e.g., source 1 has a confidence of 80%; source 2 has a confidence of 90%; confidence of the derivation is 95%; accordingly, the confidence of the data is 68.4%.

In one exemplary embodiment, confidence may be discrete at each level. Accordingly, where confidence also is attached to each piece of data, it is possible to propagate confidence at each step of data derivation. Further, this approach also enables the setting of a confidence threshold below which additional data no longer is derived.

Figure 11:
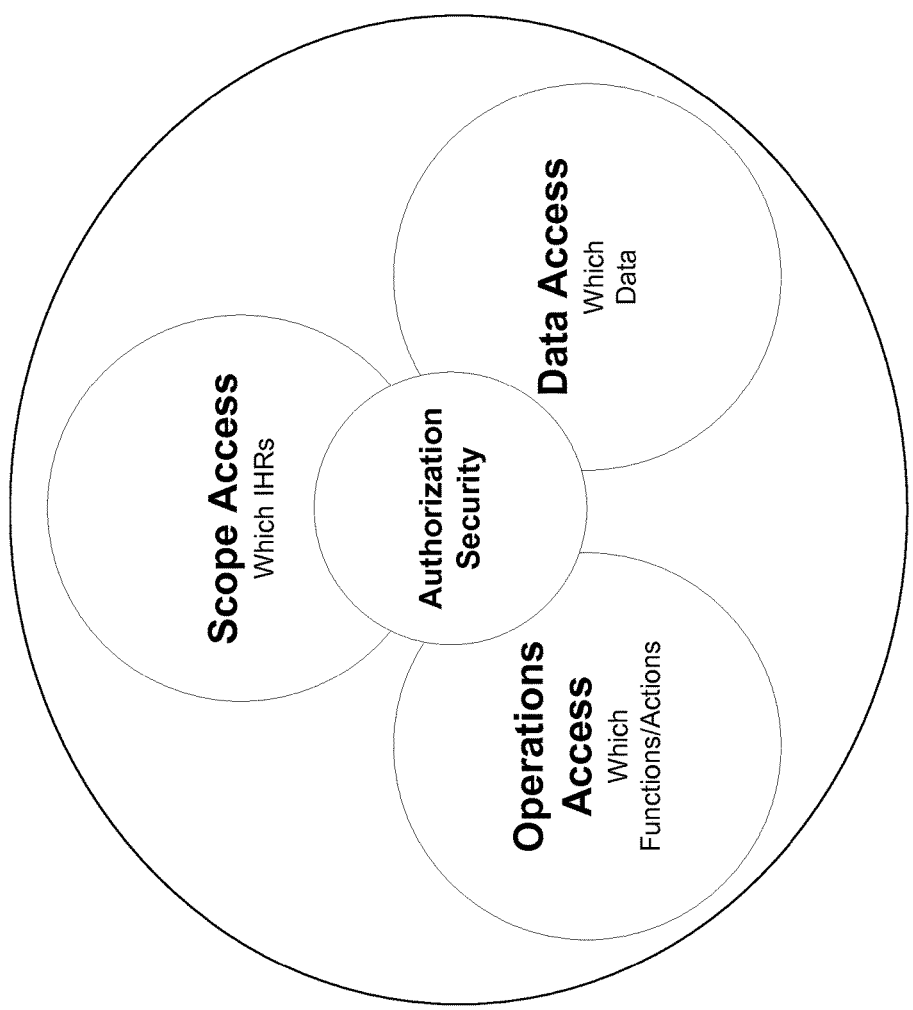
FIG. 11 is a diagram showing authorization rights components in accordance with an exemplary embodiment of the present invention.

In another exemplary embodiment, the IHR system comprises security custodial services. Prior art security models are premised on having a known, predictable pattern of system use, user types, and data—all installed in an environment where certain limitations can be imposed by and on the data custodian. In addition, security models in the prior art are too structured and rigid to work in an environment where many classes of users use the same record for different purposes. In contrast, the IHR system recognizes that neither the amount of information to be secured nor the level of detail can be presumed in advance. The IHR system is designed to deal with a variety of users, including, but not limited to, the following: patients; consumers; users who delegate their security to a custodian; and to users who come and go on the system with a need for auditing oversight but not for direct custodial intervention. The IHR system is fully adaptive: in each case, services evaluate what data to secure, what is known about the entities with potential access to this data, and what the outcome of the combination should be. As shown in FIG. 11, the authorization rights components may comprise scope access, operations access, and data access elements.

In an exemplary embodiment, data access depends on the class of data, which can include protected health information, sensitive health information, and authored protected health information. Protected health information (PHI) is used herein to refer to information that relates to the past, present, or future physical or mental health or condition of an individual, the provision of health care to an individual, or the past, present or future payment for the provision of health care to an individual, and that identifies or could reasonably be used to identify the individual. Sensitive PHI is used herein to refer to PHI that pertains to (i) an individual's HIV status or treatment of an individual for an HIV-related illness or AIDS, (ii) an individual's substance abuse condition or the treatment of an individual for a substance abuse disorder, or (iii) an individual's mental health condition or treatment of an individual for mental illness. Authored PHI is information authored by a particular user as an event initiator or performer. In various exemplary embodiment, the treatment of individual health data complies with all regulations and laws, including but not limited to HIPAA.

In one exemplary embodiment, the IHR custodial services comprise a security architecture based on relationships that the IHR system knows and/or can infer between and among entities (e.g., person to person, person to organization, and organization to organization). What an IHR system user can access, called "scope," is dynamically redefined as more and more data is known about an individual. As data is received from messages and other sources, including but not limited to direct data entry or network or Web service interactions with source systems, the relationships between entities are gleaned, codified, and used to maintain the best known information about that relationship. So, all of the relevant connections are recorded and summarized into the SBR of each relationship.

When a user accesses an IHR system access point, such as a health portlet, the scope defined in the user's set of rights is evaluated. When the user performs an operation, only the data and information of the health records that match the relationship parameters are returned.

Figure 12:
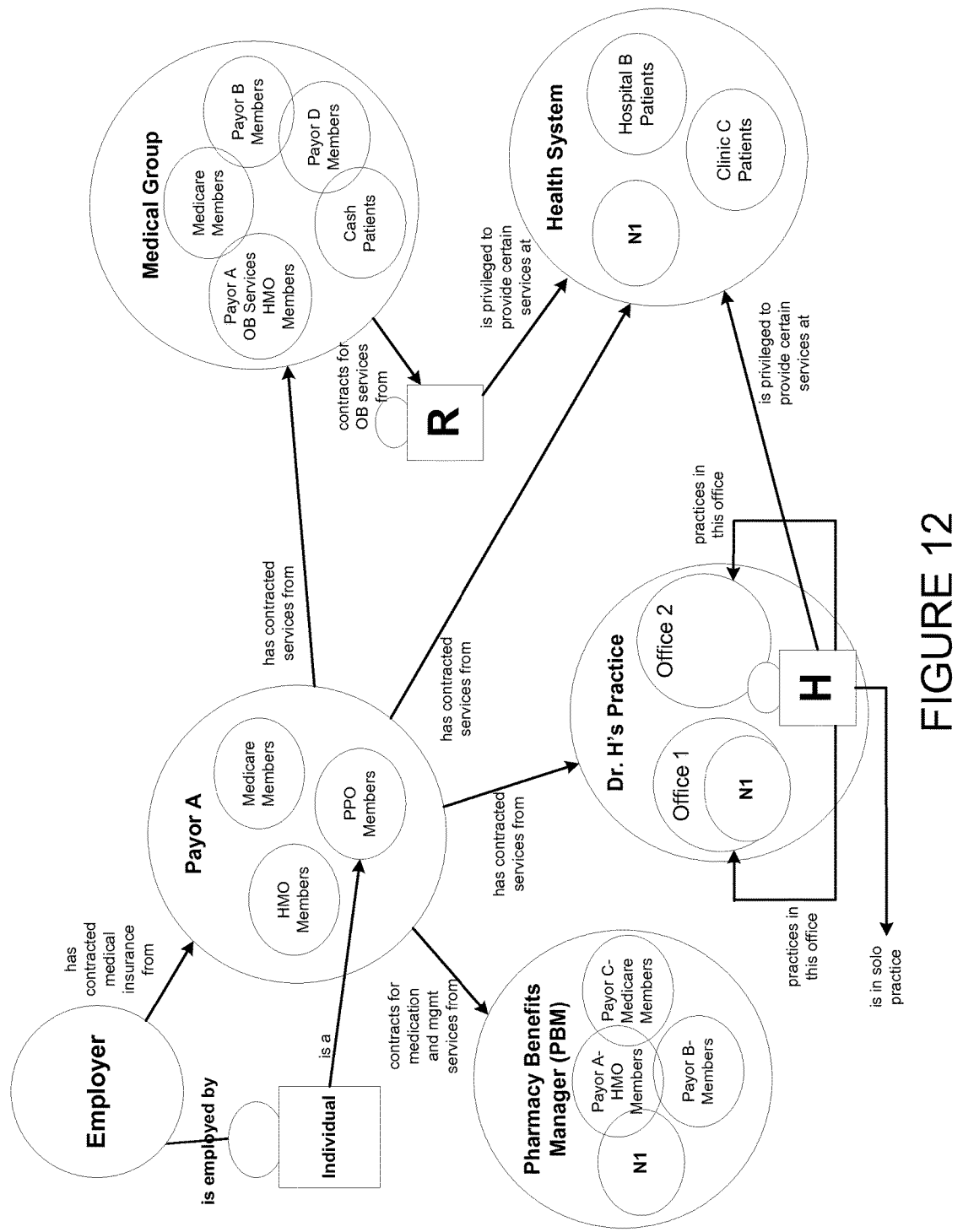
FIG. 12 is a schematic diagram of an example of individual's care relationships.

Scope of access is based on the user's relationship to the individual. An example of an individual's care relationships is shown in FIG. 12. Only users with a "legitimate relationship" with the individual will have access to records concerning the individual. In one exemplary embodiment, a legitimate relationship in the IHR system is a health relationship. A relationship-based approach allows security constraints and permissions to be defined as policies. For example, one policy might be: "provider office staff can only write prescriptions on their patients or patients associated with their practice." Thus, as the care relationships are established, maintained or terminated, the appropriate access is automatically enforced.

The security architecture comprises a number of other unique custodial services. Prior art systems often overlook that in health systems, security should be performed at the data element level, not the record level, and thus either restrict complete access to a patient's data, or restrict access to a complete class of patient information (e.g., insurance information). What is needed is the ability to restrict to any element (e.g., medical concept) of patient information. The IHR security architecture is able to restrict around particular concepts or CHIDs, or the values of a field or data element, or some combination thereof. This permits the system to restrict access or the display of any attribute of an object based on the attributes of a CHID (or other value) defined in the ontology.

Figure 13:
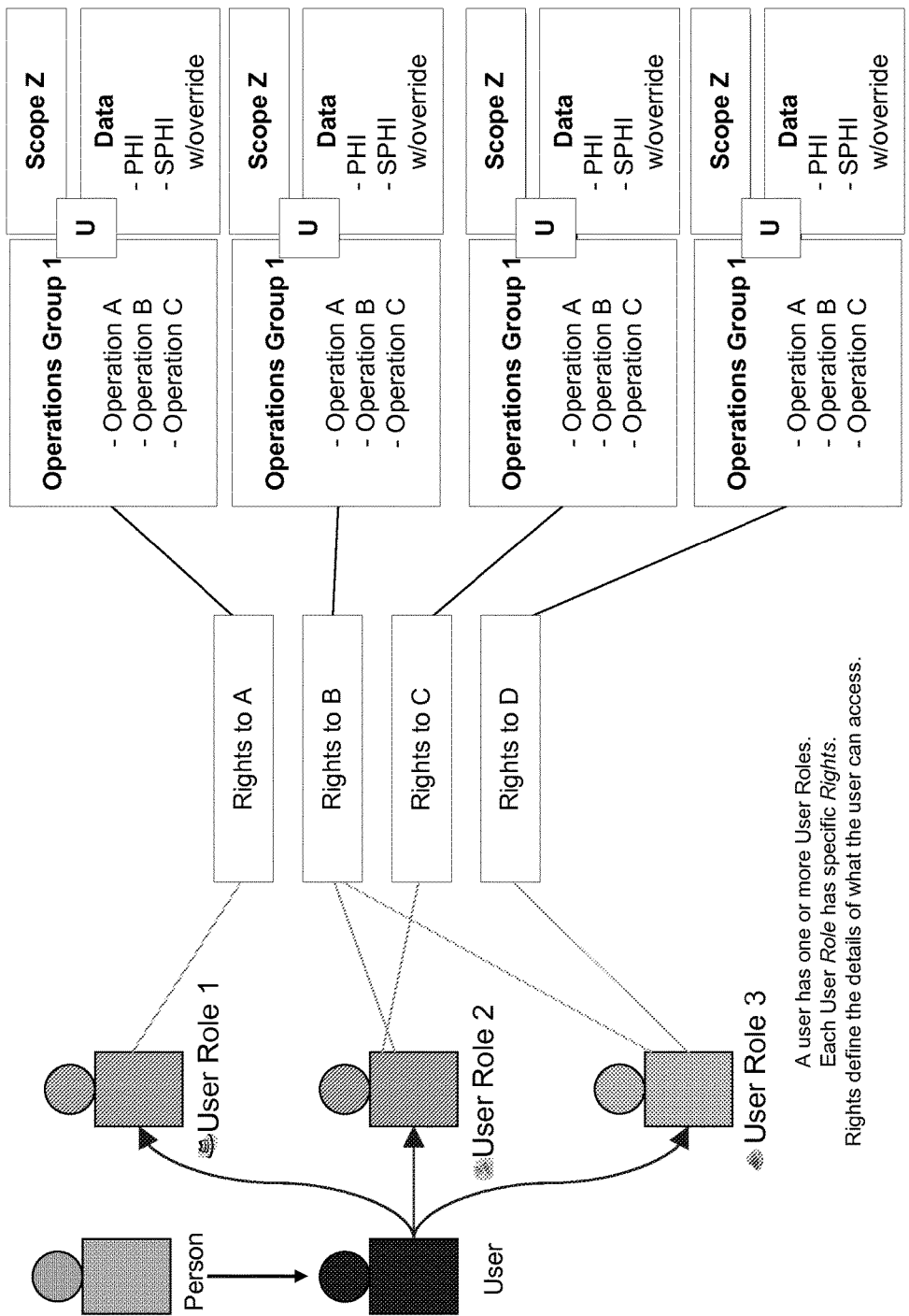
FIG. 13 shows role-based user authorization security components in accordance with an exemplary embodiment of the present invention.
Figure 14:
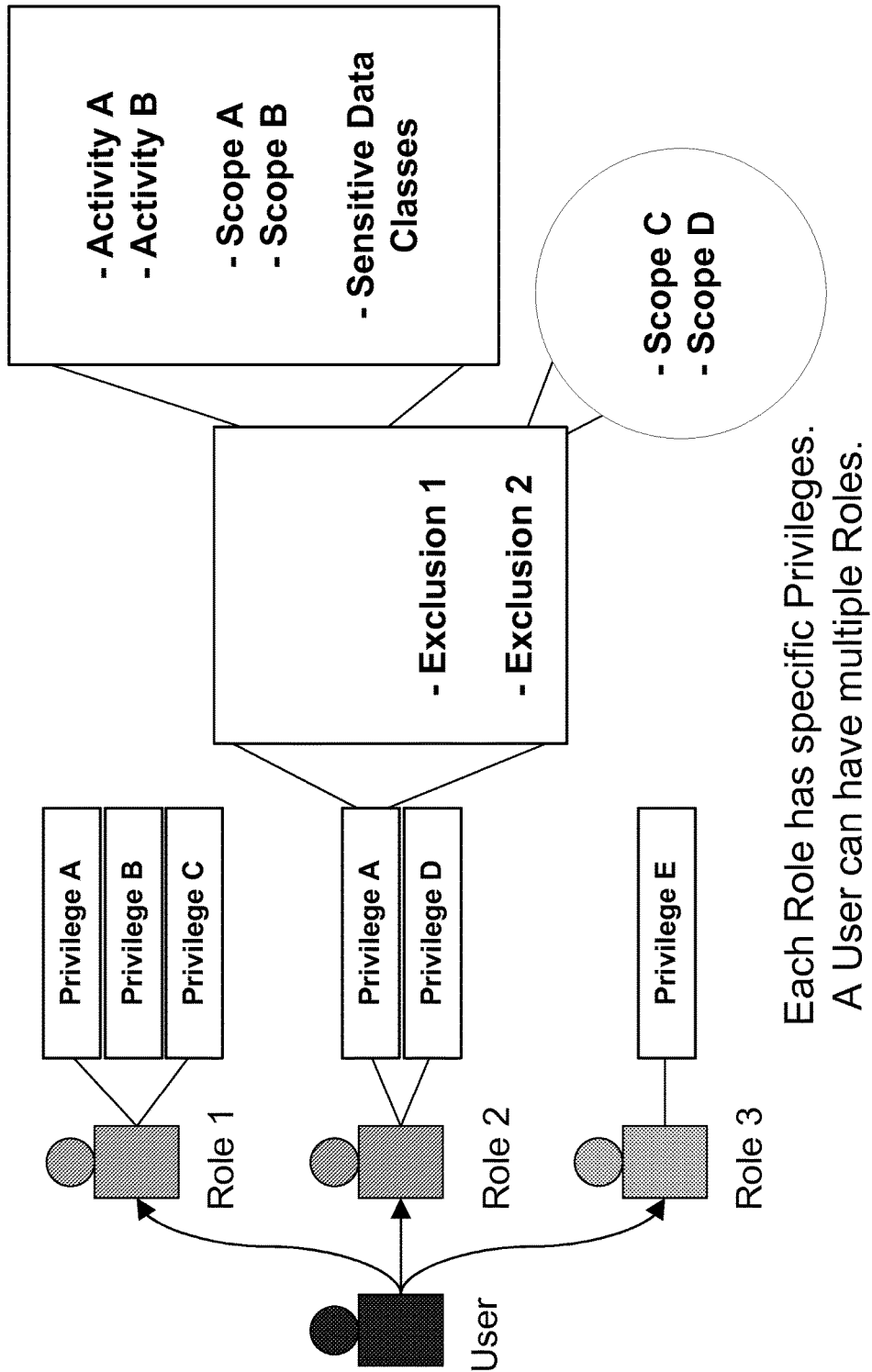
FIG. 14 shows role-based user authorization security components in accordance with an exemplary embodiment of the present invention.
Figure 15:
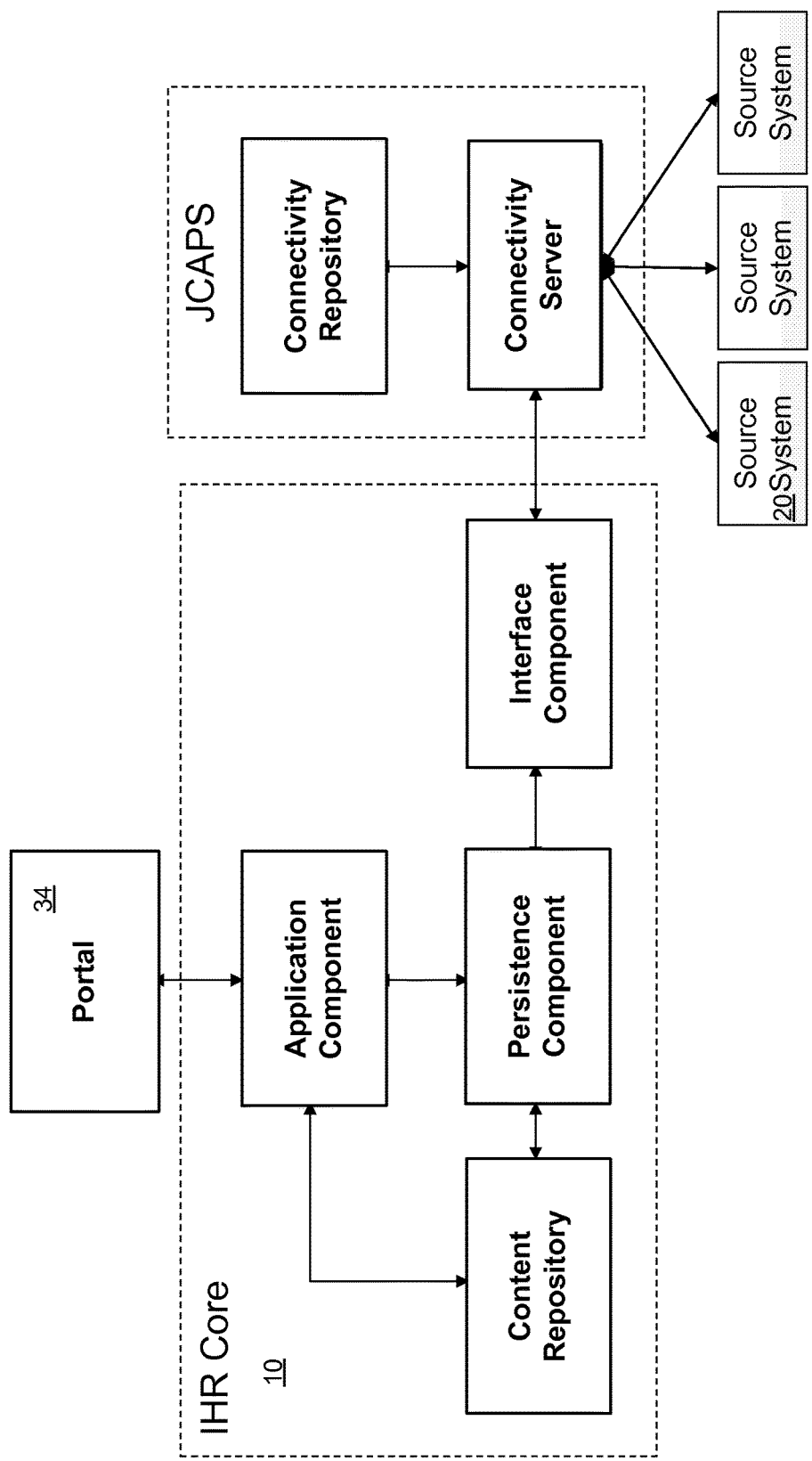
FIG. 15 is a diagram showing elements of an appliance in accordance with an exemplary embodiment of the present invention.
Figure 16:
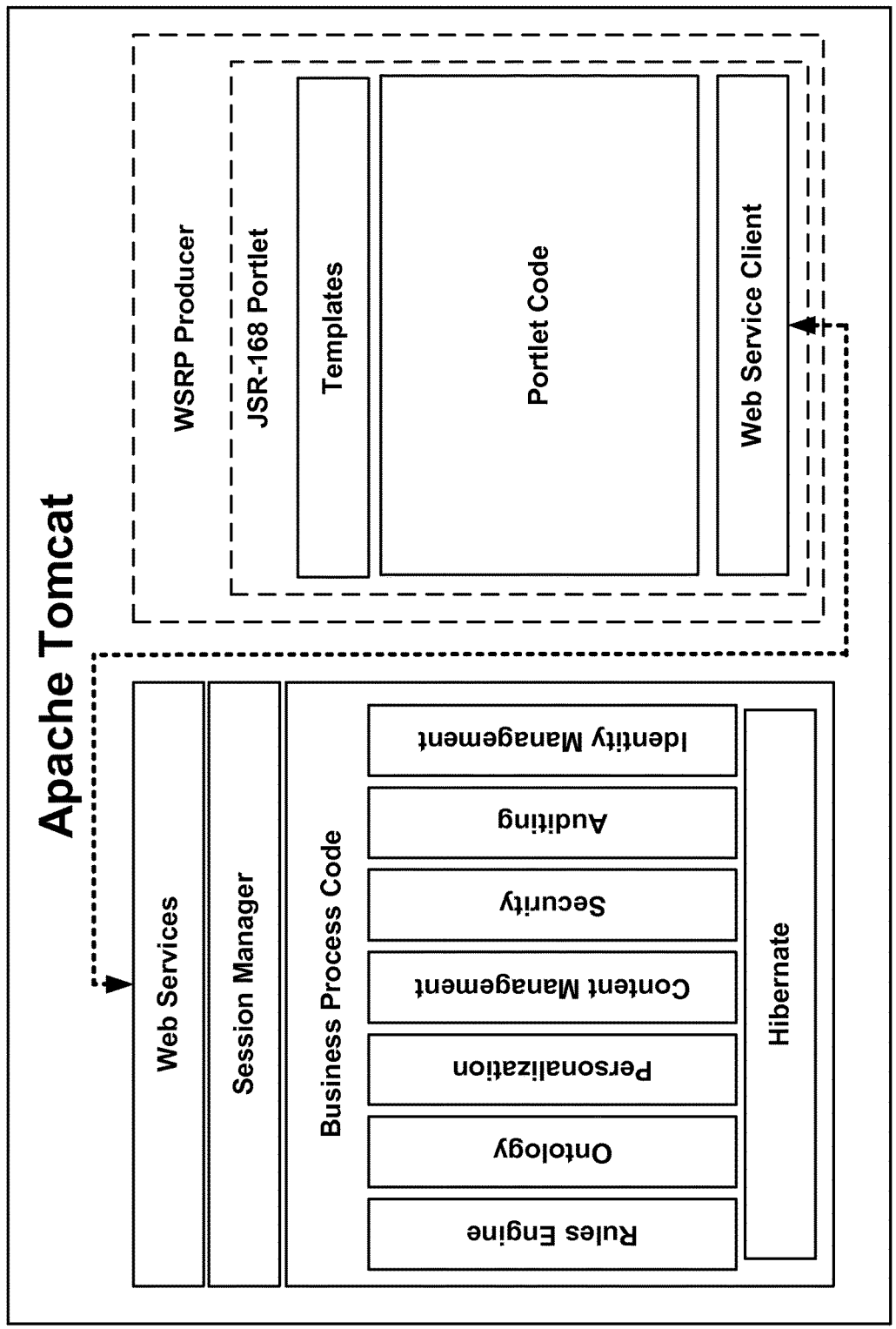
FIG. 16 is a diagram showing elements of an application server in accordance with an exemplary embodiment of the present invention.

In yet another exemplary embodiment, as seen in FIGS. 13 and 14, the IHR system comprises a multi-tiered, non-hierarchical ability to restrict access or display based on the role of a user. Role refers to the function or responsibility assumed by a person in the context of a healthcare event. Role information documents a person's association with an identified healthcare activity. Roles include, but are not limited to, provider roles (e.g., admitting, attending, billing, consulting, collaborating, interpreting, performing, referring, servicing, supervising, treating), personal roles (self, next-of-kin, emergency contact, guarantor, guardian), or organization roles (carrier, employee, employer, insured, subscriber). A user can have multiple roles 120, 121, 122, and each role can have specific rights 124, 125, 126, 127 associated with it. When the user's role or "hat" changes, the user's authorization rights change. This include scope access rights, operations access rights, and data access rights. Thus, for example, a doctor in his or her practice has different access rights than the same doctor looking at his or her own records, or the same doctor acting as a health insurance company review physician. Similarly, an individual may grant or restrict access to any or all portions of their IHR from any and all caregivers, based on a class of information (including sensitive personal health information, such as, but not limited to, psychiatric information, substance abuse information, HIV status, AIDS data, and the like). Authorized users may "break the seal" on restricted information in emergencies if that is the appropriate disposition.

Similarly, the system may permit local security administration. Each practice or distinct business entity can add and inactivate staff, and assign user roles. Further, an authorized user can delegate rights to other users, subject to the policies established by the custodian of the data.

The present invention provides a variety of ways and means to interact with the information in the IHR, including, but not limited to, through health portals, portlets, and web services. Thus, the invention provides a complete suite of information services and not just an end-user application. This allows the invention to support existing information systems in ways that previous "records" art could not. In one exemplary embodiment, Java standard portlets and web services are used to deliver a user interface (and user interaction) through a standard portal. A portal is a Internet based application, and serves as a starting point or gateway to other resources or applications. Portlets are user interface components or modules for a portal. Traditionally, portlets were custom applications for specific portals, although recently, portlet standards (such as JSR 168) have been defined. All interaction takes place via a communications chain extending from the portal through a portlet through the Internet service through the IHR application server. This system promotes flexibility and broad, cross-platform ubiquity in terms of accommodating users.

Connections between the IHR system and IHR portals and portlets may be encrypted. In one exemplary embodiment, a standard Internet Web browser is used to access the portal and portlets, and the connections are 128-bit SSL-encrypted connections. In addition, the support connection to all custodial sites will be via a VPN using encryption and other security mechanisms to ensure that only authorized users can access the network, and that data cannot be intercepted.

Administrative services include the backing up of various components of the system, including but not limited to database files and journal queues. Backup may be performed in stages, with frequent backups to intermediate storage, and less frequent backups to long-term storage. Disaster recovery operations and fail-over database servers also may be used for data and system security and continued operations.

In an exemplary embodiment, the IHR system is bundled into a prepackaged, self-contained package or "appliance," as shown in FIGS. 3, 15, 17 and 22. The IHR appliance is designed to "plug and play" in existing health care information technology systems and networks, with minimal effort and intervention. The appliance may be installed behind a network firewall. Information is obtained from all available source systems and dynamically constructed into the IHR. This appliance model for an application level solution at this level is new, and provides the ability to deliver any number of appliances and have them provide the IHR functions with minimal user intervention. In addition, this model permits appliances to be added to any node as necessary to deal with increases in volume without major re-architecting of the solution or the node. This allows rapid distribution and redeployment of IHR systems.

The IHR system thus allows individuals to understand and participate in their health care, and enables caregivers and consumers to collaborate and interact using the same record in different ways. It embraces the emerging roles of custodian and health care advocate, and assists health care stakeholders, including but not limited to health systems, health plans, IPAs, RHIOs, employers, providers, and individuals, to meet the requirements and needs for health care systems going forward into the future. In one exemplary embodiment, the present invention does not replace existing information systems and infrastructure; instead, it provides a standards-based, service-oriented infrastructure that rapidly and easily provides health-related information and components that work with such existing systems.

Operations available to users in various exemplary embodiments include, but are not limited to, identifying individuals, viewing an event list, filtering events, detailing events, editing events, printing events, viewing event details, managing users (e.g., adding users, editing users, editing user fields, deactivating users, identifying users), identifying individuals, and manipulating health issues (e.g., filtering, viewing list, viewing detail, adding, editing, and printing health issues).

In another exemplary embodiment, the system may be used for collaborative health and disease management. Over 80% of all health care costs are accrued by individuals with chronic diseases. Such diseases are difficult to manage, often requiring multiple providers caring for different issues caused by such conditions. Further complicating the care of chronic disease is the fact that the disease does not resolve (usually for the remaining lifetime of the individual) yet the individual primarily lives his or her life away from the health care system. The IHR system provides a single platform for all of a patient's care with regard to any number of chronic conditions to be coordinated and managed by any number of providers of care and non-professional caregivers, with all being continuously informed of the actions of the others and the impact such actions have on the aggregate care of the patient in the context of each provider's individual care. Further, the patient is directly involved in the management and coordination of their chronic disease care because they are a key participant in the system, both using it to learn what they should be doing as well as documenting the successful or unsuccessful completion thereof. This provides essential coordination during the 99%+ of the time when the patient is not interacting with the health care system. Finally, most chronic diseases are related to lifestyle choices. The system supports the collaboration it takes not just to managed disease, but also to managed the kinds of lifestyle changes that help prevent disease.

Thus, it should be understood that the embodiments and examples have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

We claim:

1. A computer-implemented method for processing, storing and handling health care information, comprising the steps of:
   receiving, in a self-contained, plug-and-play appliance device adapted to be incorporated into an existing network or information technology system, data or information relating to a patient's or individual's health from one or more information sources, said data comprising data in any form;
   parsing some or all of the received data or information to identify elements of the data or information;

transforming or normalizing some or all of the received data or information, and some or all of the parsed data elements, to created transformed or normalized data elements;

assigning a confidence indicator or weight to the transformed or normalized data elements, wherein said confidence indicator is a value in a non-binary range;

mapping the transformed or normalized data elements in accordance with an ontology;

obtaining a first set of matching criteria rules that identify whether the transformed or data elements sufficiently match an existing health care object as a function of one or more person or entity criteria;

automatically determining whether to create a new health care object or modify an existing health care object based on the outcome of application of the first set of matching criteria rules;

automatically modifying an existing health care object or creating anew health care object from said transformed or normalized data elements based on the outcome of said determination step, wherein said existing or new health care object is an object-oriented software environment object subject to an object hierarchy;

automatically obtaining and applying a second set of rules specifying time-dependent criteria for scheduling healthcare events every time said new health care object is created or said existing health care object is modified; and storing the mapped data elements in a data store in accordance with a health information model, wherein said health information model associates the patient or individual with a patient or individual record, said record comprising:

identification information for one or more third parties associated with providing healthcare for the patient or individual;

health condition and health service information for the patient or individual, including timeline information;

medication information for the patient or individual;

lifestyle information for the patient or individual;

health treatment, monitoring and encounter information for the patient or individual; and medical findings and measure data for the patient or individual.

2. The method of claim 1, further comprising the steps of:
receiving data or information relating to a health condition, service, product, treatment or encounter for the patient or individual; and
determining healthcare decisions, diagnoses or treatment for said patient or individual based upon the data or information relating to a health condition, service, product, treatment or encounter, and the mapped data elements stored in a data store in accordance with the health information model.

3. The method of claim 1, further comprising the steps of:
receiving data or information relating to a plurality of health services performed for or provided to the patient or individual; and
determining, based upon the mapped data elements stored in a data store in accordance with the health information model, whether any one or more of said plurality of health services is related to or associated with one or more health conditions of the patient or individual.

4. The method of claim 3, further comprising the step of creating a timeline of health services or events related to or associated with the patient or individual, based upon information in the patient or individual's health record.

5. The method of claim 2, wherein the step of mapping the transformed or normalized data elements in accordance with an ontology is performed using one or more code sets, vocabularies, or rule sets; and
further wherein the one or more code sets, vocabularies, or rule sets are updated, modified, or extended based upon the healthcare decision, diagnosis or treatment determination.

6. The method of claim 1, wherein the transformed or normalized data elements comprise standardized healthcare diagnostic, treatment and management codes.

7. The method of claim 1, wherein the transformed or normalized data elements comprise standardized healthcare or clinical terms and classifications.

8. The method of claim 1, wherein the transformed or normalized data elements comprise standardized medical findings and measure terms and units.

9. The method of claim 1, wherein the confidence indicator or weight is based on the identity of the source of information or data.

10. The method of claim 1, wherein the confidence indicator or weight is based on history and amount of processing required, and how and when the information or data is received; and
further wherein the confidence indicator or weight is adjusted over time.

11. The method of claim 1, wherein the confidence indicator or weight is based on the relevance of the data in relation to an ontology.

12. A non-transitory computer-readable storage medium in a self-contained, plug-and-play appliance device adapted to be incorporated into an existing network or information technology system, storing instructions that cause a microprocessor or processor to perform the following steps:

receiving, in the self-contained, plug-and-play appliance device, data or information relating to a patient's or individual's health from one or more information sources, said data comprising data in any form;

parsing some or all of the received data or information to identify elements of the data or information;

transforming or normalizing some or all of the received data or information, and some or all of the parsed data elements, to created transformed or normalized data elements;

assigning a confidence indicator or weight to the transformed or normalized data elements, wherein said confidence indicator is a value in a non-binary range;

mapping the transformed or normalized data elements in accordance with an ontology;

obtaining a first set of matching criteria rules that identify whether the transformed or data elements sufficiently match an existing health care object as a function of one or more person or entity criteria;

automatically determining whether to create a new health care object or modify an existing health care object based on the outcome of application of the first set of matching criteria rules;

automatically modifying an existing health care object or creating a new health care object from said transformed or normalized data elements based on the outcome of said determination step, wherein said existing or new health care object is an object-oriented software environment object subject to an object hierarchy;

automatically obtaining and applying a second set of rules specifying time-dependent criteria for scheduling healthcare events every time said new health care object is created or said existing health care object is modified; and storing the mapped data elements in a data store in accordance with a health information model, wherein said health information model associates the patient or individual with a patient or individual record, said record comprising:

identification information for one or more third parties associated with providing healthcare for the patient or individual;

health condition and health service information for the patient or individual, including timeline information;

medication information for the patient or individual;

lifestyle information for the patient or individual;

health treatment, monitoring and encounter information for the patient or individual; and medical findings and measure data for the patient or individual.

13. The medium of claim 12, further wherein the microprocessor or processor is caused by the instructions to perform the following steps:

receiving data or information relating to a health condition, service, product, treatment or encounter for the patient or individual; and determining healthcare decisions, diagnoses or treatment for said patient or individual based upon the data or information relating to a health condition, service, product, treatment or encounter, and the mapped data elements stored in a data store in accordance with the health information model.

14. The medium of claim 12, further wherein the microprocessor or processor is caused by the instructions to perform the following steps:

receiving data or information relating to a plurality of health services performed for or provided to the patient or individual; and determining, based upon the mapped data elements stored in a data store in accordance with the health information model, whether any one or more of said plurality of health services is related to or associated with one or more health conditions of the patient or individual.

15. The medium of claim 14, further wherein the microprocessor or processor is caused by the instructions to perform the step of creating a timeline of health services or events related to or associated with the patient or individual, based upon information in the patient or individual's health record.

16. The medium of claim 13, wherein the step of mapping the transformed or normalized data elements in accordance with an ontology is performed using one or more code sets, vocabularies, or rule sets; and further wherein the one or more code sets, vocabularies, or rule sets are updated, modified, or extended based upon the healthcare decision, diagnosis or treatment determination.

17. The medium of claim 12, wherein the transformed or normalized data elements comprise one or more of the following:

standardized healthcare diagnostic, treatment and management codes;

standardized healthcare or clinical terms and classifications; or standardized medical findings and measure terms and units.

18. The medium of claim 12, wherein the confidence indicator or weight is based on one or more of the following:

the identity of the source of information or data;

the history and amount of processing required, and how and when the information or data is received, wherein the confidence indicator or weight is adjusted over time; or the relevance of the data in relation to an ontology.

19. A system for processing, storing and handling health care information, comprising:

a self-contained, plug-and-play appliance device adapted to be incorporated into an existing network or information technology system, said appliance device comprising one or more microprocessors or processors operatively coupled to a memory, said memory operable to store at least one program, said program, when executed by said one or more microprocessors or processors, causing the one or more microprocessors or processors to:

receive data or information relating to a patient's or individual's health from one or more information sources, said data comprising data in any form;

parse some or all of the received data or information to identify elements of the data or information;

transform or normalize some or all of the received data or information, and some or all of the parsed data elements, to created transformed or normalized data elements;

assign a confidence indicator or weight to the transformed or normalized data elements, wherein said confidence indicator is a value in a non-binary range;

map the transformed or normalized data elements in accordance with an ontology;

obtain a first set of matching criteria rules that identify whether the transformed or data elements sufficiently match an existing health care object as a function of one or more person or entity criteria;

automatically determine whether to create anew health care object or modify an existing health care object based on the outcome of application of the first set of matching criteria rules;

automatically modify an existing health care object or create a new health care object from said transformed or normalized data elements based on the outcome of said determination step, wherein said existing or new health care object is an object-oriented software environment object subject to an object hierarchy;

automatically obtain and apply a second set of rules specifying time-dependent criteria for scheduling healthcare events every time said new health care object is created or said existing health care object is modified;

and store the mapped data elements in a data store in accordance with a health information model, wherein said health information model associates the patient or individual with a patient or individual record, said record comprising:

identification information for one or more third parties associated with providing healthcare for the patient or individual;

health condition and health service information for the patient or individual, including timeline information;

medication information for the patient or individual;

lifestyle information for the patient or individual;

health treatment, monitoring and encounter information for the patient or individual; and medical findings and measure data for the patient or individual.

20. The system of claim 19, further wherein the microprocessor or processor is caused by the program to:
receive data or information relating to a health condition, service, product, treatment or encounter for the patient or individual; and
determine healthcare decisions, diagnoses or treatment for said patient or individual based upon the data or information relating to a health condition, service, product, treatment or encounter, and the mapped data elements stored in a data store in accordance with the health information model.

21. The system of claim 19, further wherein the microprocessor or processor is caused by the program to:
receive data or information relating to a plurality of health services performed for or provided to the patient or individual; and
determine, based upon the mapped data elements stored in a data store in accordance with the health information model, whether any one or more of said plurality of health services is related to or associated with one or more health conditions of the patient or individual.

22. The system of claim 21, further wherein the microprocessor or processor is caused by the program to create a timeline of health services or events related to or associated with the patient or individual, based upon information in the patient or individual's health record.

23. The system of claim 20, wherein the mapping the transformed or normalized data elements in accordance with an ontology is performed using one or more code sets, vocabularies, or rule sets; and
further wherein the one or more code sets, vocabularies, or rule sets are updated, modified, or extended based upon the healthcare decision, diagnosis or treatment determination.

24. The system of claim 19, wherein the transformed or normalized data elements comprise one or more of the following:
standardized healthcare diagnostic, treatment and management codes;
standardized healthcare or clinical terms and classifications; or
standardized medical findings and measure terms and units.

25. The system of claim 19, wherein the confidence indicator or weight is based on one or more of the following:
the identity of the source of information or data;
the history and amount of processing required, and how and when the information or data is received, wherein the confidence indicator or weight is adjusted over time; or
the relevance of the data in relation to an ontology.

* * * * *

UNITED STATES PATENT AND TRADEMARK OFFICE
CERTIFICATE OF CORRECTION

PATENT NO.        : 10,460,841 B2
APPLICATION NO.   : 14/308873
DATED             : October 29, 2019
INVENTOR(S)       : Korpman et al.

Page 1 of 1

It is certified that error appears in the above-identified patent and that said Letters Patent is hereby corrected as shown below:

In the Claims

Column 21
Line 19, "anew" should read --a new--

Column 24
Line 36, "anew" should read --a new--

Signed and Sealed this
Tenth Day of December, 2019

Andrei Iancu
*Director of the United States Patent and Trademark Office*